(12) United States Patent
Cormack et al.

(10) Patent No.: US 9,029,473 B2
(45) Date of Patent: May 12, 2015

(54) FUNCTIONALISED POLYMERS FOR BINDING METAL SURFACES

(75) Inventors: Peter Cormack, Strathclyde (GB); Duncan Graham, Strathclyde (GB); Aaron Hernandez-Santana, Strathclyde (GB); Arun Prasath Ramaswamy, Sydney (AU); William Ewen Smith, Strathclyde (GB)

(73) Assignee: University of Strathclyde, Glascow, Strathclyde (GB)

( * ) Notice: Subject to any disclaimer, the term of this patent is extended or adjusted under 35 U.S.C. 154(b) by 0 days.

(21) Appl. No.: 12/446,817

(22) PCT Filed: Oct. 23, 2007

(86) PCT No.: PCT/GB2007/004038
§ 371 (c)(1), (2), (4) Date: Apr. 23, 2009

(87) PCT Pub. No.: WO2008/050109
PCT Pub. Date: May 2, 2008

(65) Prior Publication Data
US 2010/0035359 A1     Feb. 11, 2010

(30) Foreign Application Priority Data

Oct. 23, 2006   (GB) .................................. 0621050.4

(51) Int. Cl.
| | |
|---|---|
| *G01N 21/65* | (2006.01) |
| *C08F 8/00* | (2006.01) |
| *C08F 283/00* | (2006.01) |
| *C08G 63/91* | (2006.01) |
| *C08F 283/12* | (2006.01) |

(Continued)

(52) U.S. Cl.
CPC ............ *B22F 1/0018* (2013.01); *G01N 21/658* (2013.01); *G01N 21/65* (2013.01); *B22F 1/0062* (2013.01); *B22F 1/0096* (2013.01); *B82Y 30/00* (2013.01); *B22F 2998/00* (2013.01); *C08F 2800/20* (2013.01)

(58) Field of Classification Search
None
See application file for complete search history.

(56) References Cited

U.S. PATENT DOCUMENTS

| | | | |
|---|---|---|---|
| 4,619,990 | A | 10/1986 | Elmasry |
| 4,859,759 | A | 8/1989 | Maycock et al. |

(Continued)

FOREIGN PATENT DOCUMENTS

| | | |
|---|---|---|
| WO | 03/038436 | 5/2003 |
| WO | 2006/084650 | 8/2006 |

OTHER PUBLICATIONS

Ahlheim, M. et al. "Electrooptically active polymers. non-linear optical polymers prepared from maleic anhydride copolymers by polymer analogous reactions," Macrol. Chem. Phys. 195, 361-373 (1994).*

(Continued)

*Primary Examiner* — Yelena G Gakh
*Assistant Examiner* — Michelle Adams
(74) *Attorney, Agent, or Firm* — Valauskas Corder LLC

(57) ABSTRACT

Disclosed are polyvalent macromolecules, compositions comprising the macromolecules, and methods of use. The polyvalent macromolecules have a polymer backbone and pendent groups attached to the polymer backbone. Some or all of the pendent groups have optionally a linker, a surface-seeking group capable of binding strongly to a metal surface, and a spectroscopically detectable chromophore detectable.

22 Claims, 12 Drawing Sheets

(51) Int. Cl.
*C08F 283/02* (2006.01)
*C08G 18/00* (2006.01)
*B32B 15/08* (2006.01)
*B32B 15/02* (2006.01)
*C08K 3/08* (2006.01)
*B22F 1/00* (2006.01)
*B82Y 30/00* (2011.01)

(56) References Cited

U.S. PATENT DOCUMENTS

| | | | |
|---|---|---|---|
| 5,206,378 | A | 4/1993 | Macleay et al. |
| 6,750,065 | B1* | 6/2004 | White et al. ............... 436/518 |
| 2003/0157038 | A1 | 8/2003 | Candau |
| 2005/0130163 | A1* | 6/2005 | Smith et al. ............... 435/6 |

OTHER PUBLICATIONS

Wickham, D. T. et al. "Adsorption of Nitrogen Dioxide on Polycrystalline Gold," Catalysis Letters 1990, 6, 163-172.*
Graham, D. et al. "Biosensing using silver nanoparticles and surface enhanced resonance Raman scattering," Chem. Commun. 2006, 4363-4371; published online Aug. 9, 2006.*
Diduch, K. et al. "Photocurrent generation of bi-functional carbazole containing polymers," Synthetic Metals 139 (2003) 515-520.*
McCabe, A. et al. "Remote Detection Using Surface-Enhanced Raman Scattering," Applied Spectroscopy 56 (2002) 820-826.*
Cunningham, D. et al., "Practical control of SERRS enhancement," Faraday Discussions, Royal Society of Chemistry (2005) 132:135-145.
Luxenhofer, R. et al., "Click chemistry with poly(2-oxazoline)s," Macromolecules (2006) 39(10):3509-3516.
Sun, B. et al., "A novel synthetic method for well-defined polymers containing benzotriazole and diazobenzene chromophores," Macromol. Chem. Phys. (2007) 208(10):1101-1109.
Yoshida, S. et al., "Functional polymers. XIII. Synthesis and polymerization of 2(2-hydroxy-5-methylphenyl)-5-vinyl-2H-benzotriazole," J. Polymer Sci.: Polymer Chem. Ed. (1982) 20(8):2215-2230.
International Search Report and Written Opinion for Application No. PCT/GB2007/004038 dated Apr. 15, 2008 (9 pages).
International Preliminary Report on Patentability for Application No. PCT/GB2007/004038 dated Apr. 28, 2009 (13 pages).
Li, X. et al. "Fluorescent Poly(Arylene Ether)s with a 3,5-Dipyridyl-1,2,4-triazole Pendent Group Joined by N-N Linkage" Journal of Macromolecular Science (2006) 43: 1279-1291.
Graham, D. et al. "SERRS detection of PNA and DNA labelled with a specifically designed benzotriazole azo dye" Chemcomm (2001) 10:1002-1003.
Mayer, A et al. "Colloidal Gold Nanoparticles Protected by Water-Soluble Homopolymers and Random Copolymers" Eur. Polym. (1998) 34(1): 103-108.
McCabe, A. et al. "SERRS labelled beads for multiplex detection" Faraday Discuss (2006) 32: 303-308.
Chen, Y. et al. "Gold and silver nanoparticles functionalized with known numbers of oligonucleotides per particle for DBA detection" Chem. Commun. (2004): 2804-2805.
Alli, A. et al. "Poly(arylene ether)s Containing 1,2,4-Triazole and Phthalimide or Naphthalimide Moieties Joined by a N-N Linkage" MAcromolecules (2002) 35: 8728-8737.

* cited by examiner (a)

(b)

Mass spectrum of Polymerisable dye M/z (LC/DI) 444.20

FUNCTIONALISED POLYMERS FOR BINDING METAL SURFACES

CROSS-REFERENCE TO RELATED APPLICATIONS

This patent application is a national stage filing under 35 U.S.C. 371 of International Application No. PCT/GB2007/004038, filed on Oct. 23, 2007, which claims foreign priority benefits to United Kingdom Patent Application No. 0621050.4, filed on Oct. 23, 2006. These applications are incorporated herein by reference in their entireties.

TECHNICAL FIELD

This invention relates to methods of binding (e.g. protecting and labelling) metal surfaces, to methods for inducing and controlling aggregation of metal nanoparticles, and to bioassays involving labelled surfaces.

BACKGROUND OF THE INVENTION

Metal nanoparticles have a wide variety of applications in biomedical applications and in particular in biological labelling and detection techniques. For example, ligand-functionalised magnetic nanoparticles (for example iron oxide nanoparticles) are used in cell separation and probing (Ref: Pankhurst et al, *J. Phys. D: Appl. Phys.*, 2003, 36, R167-R181) and gold nanoparticles have been widely used in immunohistochemistry to identify protein-protein interaction.

One technique which utilises metal nanoparticles is Surface Enhanced Raman Spectroscopy (SERS) and the related technique Surface Enhanced Resonance Raman Spectroscopy (SERRS). SERRS is an extraordinarily sensitive and information-rich spectroscopic method that relies upon the surface-enhancement of the in resonance Raman scattering of a reporter molecule (dye) localised on a suitable metallic substrate, e.g., silver or gold (Ref: Munro et al, *Langmuir*, 1995, 11, 3712). The present inventors have previously disclosed the use of SERRS techniques for the detection and identification of nucleic acid sequences. For example, WO 97/05280 and 99/60157 disclose methods and materials for detecting or identifying particular nucleic acid sequences in a sample using SERRS. The sample is exposed to a detection agent comprising a colloid metal surface associated with a SERRS active species (SAS) such as an azo dye, and with a target binding species (TBS) which is complementary to the target. The sample/agent mixture is observed to detect any surface enhancement of the label. Generally a surface-seeking group such as the benzotriazole group is used to promote chemisorption of the SAS and/or TBS to the metal surface.

In techniques using nanoparticles, it is often desirable to control the degree to which the metal nanoparticles are aggregated. In particular, in SERRS detection, the highest possible signal enhancements are realised only when the particles are aggregated, as it is the high electric field gradients generated at the junctions of the aggregated particles that are believed to be responsible for the highest signal enhancements (Ref: Moskovits, *Rev. Mod. Phys.*, 1985, 57, 783). It is therefore advantageous to have a high degree of control over the extent to which aggregation occurs (Ref: Khan et al, *Faraday Discuss.*, 2006, 132, 171).

Individual nanoparticles can be induced to aggregate by the addition of aggregating agents such as sodium chloride, or by the addition of dyes with an affinity for the metal surface. Previously, attempts have been made to encapsulate SERRS-active nanoparticle aggregates in polymer beads (Ref: McCabe et al, *Faraday Discuss.*, 2006, 132, 303) to prevent further irreversible aggregation and thereby loss of signal intensity. However particle aggregation within each bead was variable. Besides this, no routine method for controlling the aggregation of metal nanoparticles, in particular SERRS-active metal nanoparticles, exists.

The control of aggregation of metal nanoparticles may also be of benefit in other analytical techniques. The benefits may include improvement in detection by plasmon resonance emission and absorption, and enhanced fluorescence. There are also a growing number of aggregation-dependent sensors that make use of a simple colour change in the presence of a target In addition, increasing the stability of dye-loaded, aggregated metal nanoparticles is of interest in many fields, but in particular in SERRS techniques because a stable aggregation state gives rise to a stable SERRS response. This therefore significantly extends the range of potential applications.

In addition to the above, where it is desired to bind a chromophore to a metal surface (e.g. for use as a marker, or in an assay, and irrespective of aggregation) it will generally be desirable to increase surface adhesion of the chromophore so as to reduce leaching.

Metal surfaces other than nanoparticulate surfaces may also be used in SERRS and other techniques and protection and stabilisation of these surfaces is also of great interest. Another key problem is to avoid displacement of analytes from the surface of the metals on exposure to solutes, such as sodium chloride.

DESCRIPTION OF THE INVENTION

The present invention now provides specially designed polyvalent macromolecules for the treatment of metal surfaces, to protect and/or label the metal surface. In preferred forms the methods and materials disclosed herein may be used to conveniently bind known or novel chromophores to metal surfaces without the need to establish complex, bespoke, chemistry.

The method may also be particularly useful for the stabilisation and labelling of metal nanoparticles, and also serves as a means for aggregating nanoparticles in a controlled fashion.

The new macromolecules are based on a novel concept. They consist of a polymer chain with one or more surface-seeking groups ('SSG') tethered to the polymer (e.g. on side chains). Such materials can be prepared either by the chemical modification of pre-formed polymers or via the polymerisation of monomers containing the surface-seeking groups. The polymer chains can be linear or non-linear (e.g. dendritic) in structure, and may optionally have crosslinks, and the SSGs can be tethered to the polymer chains via covalent or non-covalent bonds. The surface-seeking groups cause adherence of the polymer to the metal surface. The result is that the polymer sits well on the metal surface. In the case of metal nanoparticle surfaces, the molecule may be able to span across two or more nanoparticles simultaneously, thus influencing and/or controlling the aggregation state.

The present inventors have also discovered that the polyvalent macromolecules of the invention form regular clusters of nanoparticles (known as 'popcorn' or 'raspberries') if added to metal colloid in certain concentrations (see FIG. 11). The size and shape of the 'popcorn' aggregates are well controlled. This does not happen if the colloid is dried out or if a monomeric dye is added.

Compared to treating the surfaces with monomeric dyes, as has been attempted previously (Ref: McCabe et al, *Faraday Discuss.*, 2006, 132, 303-308) there is greatly increased stability, both in terms of the stability of the aggregated nanoparticles and the resistivity of the system to chemical attack.

Functional groups on the polymer, which can be introduced either during the synthesis of the polymer or in a subsequent chemical modification step, can also be used to attach biomolecules, which is of great value for bio-analytical applications, such as those discussed above.

The polyvalent character of the macromolecules of the invention gives multiple point attachment of the polymer to the surface and leads to significantly-enhanced affinity for metal surfaces relative to monovalent species. The tight binding of the macromolecules to metal nanoparticles acts to stabilise colloidal aggregates against further, irreversible aggregation. In the case of SERRS-active metal nanoparticles, this has the advantage of not only giving rise to intense SERRS spectra, but also leads to exceptionally time-stable SERRS signals, even under operating conditions that would normally lead to rapid loss of signal.

Data obtained by the present inventors also demonstrates protection of the metal surfaces against unwanted attack by agents such as sodium chloride present in the surrounding medium. Finally, the macromolecules can be further modified chemically, e.g., by attachment of biomolecules or other chemical species, opening up exciting new opportunities for ultra-sensitive bioanalysis and molecular diagnostics applications.

Some particular aspects of the present invention will now be discussed in more detail.

Accordingly, an aspect of the present invention provides a polyvalent macromolecule comprising
- a polymer backbone, which may or may not be synthetic, and
- pendent groups attached to said polymer backbone, wherein some or all of said pendent groups comprise:
  - optionally a linker, which connects said pendent group to the polymer backbone;
  - a surface-seeking group (SSG), which is capable of binding to a metal surface; and
  - optionally a chromophore or other label, which is detectable by at least one spectroscopic method.

The term 'some or all' as used herein may refer to 'two or more'. The SSG and chromophore (if present) may or may not be on the same pendent groups.

Polymers

In the context of this application, the term 'polymer backbone' may refer to any polymer having suitable points of attachment for the pendent groups described above, for example functional side chains to which the pendent groups may be covalently or non-covalently bonded.

The term polymer is well known in the art, and refers to a large molecule made up of multiple repeating units (monomers). The polymers suitable for use in the invention may be linear, branched, hyperbranched or dendritic in structure, and in some embodiments, may contain cross-linking i.e. bonding between individual polymer chains. Although longer polymers are preferred (greater than 10, 20, 30, 40, 50 or 100 monomers) those skilled in the art will appreciate that even shorter molecules (oligomers, trimers, dimers) provided they comprise multiple repeating units. In certain preferred embodiments, the polymer backbone is a synthetic polymer. More preferably it is a commercially available synthetic polymer.

In this context, 'synthetic' polymers are defined as polymers which do not occur in nature, and this definition therefore specifically excludes polymeric species such as polypeptides (proteins), polysaccharides and polynucleotides. However these biopolymeric species may be suitable for use in other embodiments of the invention.

Types of polymers suitable for use as the polymer backbone in the invention include, but are not limited to: chain-growth (addition) polymers such as polyanhydrides, polymethacrylates, polyacrylates, polyacrylamides, polyhydrocarbons, polystyrenes, polyvinylchloride, polyvinylacetate, polyvinylpyrrolidone, polyethers (e.g. poly(ethylene glycol)), poly(ethylene), polycyanoacrylates and step-growth (condensation) polymers such as polyesters (e.g. polylactide, polyglycolide, polycaprolactone), polyamides, polyimides, polysiloxanes, polyorthoesters, polycarbonates, polyureas, polyurethanes, polyethylenimines, poly(vinylphenol), poly(alkylamine), poly(alkylamino)acrylates, poly(halostyrene), poly(haloalkylene), poly(acryloyl chloride), poly(ester-urethanes), poly(ether-urethanes), poly(urea-urethanes), poly(ester-ether-urethanes), poly(ester-urea-urethanes), poly(ether-urea-urethanes), poly(epichlorohydrin-ethylene oxide), poly(vinylalcohol-itaconic acid), poly(vinlyalcohol-vinylacetate), and poly(Bisphenol A-epichlorohydrin). Other examples of polymers suitable for use as the polymer backbone in the invention include: polyvinyl pyridine, polyacrylonitriles and polyallyl amines.

Polymers may be formed of more than one type of monomer, in which case they can also be referred to as co-polymers. Co-polymers may be random or non random co-polymers, e.g. block co-polymers. Co-polymers suitable for use in the invention may include co-polymers of two or more of the polymers listed above. These include, but are not limited to poly(styrene-co-nhydride)s, poly(styrene-methacrylate)s, poly(ether-esters), poly(acrylate-methacrylate), poly(ester-amide). In some embodiments of the invention it is preferred that the polymer backbone comprises a synthetic co-polymer. In certain embodiments the co-polymer may preferably be a block co-polymer. In other embodiments, the polymer may be a random co-polymer, tapered co-polymer, or a mixed block and random co-polymer.

The polymers suitable for use as the polymer backbone in the invention may be synthesized using controlled polymerisation techniques, such as controlled radical polymerisation techniques. These polymerisation techniques allow the length of the polymer backbone synthesised to be controlled, thereby leading to the preparation of polymer backbones with narrow molecular weight distributions. A further advantage of the these polymerisation techniques is that they allow the precise polymer architecture to be controlled.

Examples of controlled polymerisation techniques are Reversible Addition-Fragmentation chain Transfer (RAFT), Atom-Transfer Radical Polymerisation (ATRP) and N-oxyl-controlled free radical polymerisation. Other examples of controlled polymerisation techniques are known to persons skilled in the art.

The controlled polymerisation techniques described above may also be used to synthesise the polyvalent macromolecules of the invention using monomers, e.g. synthetic monomers. Some or all of the monomers may comprise a pendent group, which comprises a surface-seeking group (SSG) capable of binding to a metal surface. Some or all of the monomers may also comprise a pendent group comprising a chromophore, which is detectable by at least one spectroscopic method. The surface seeking group (SSG) and the chromophore may be present on the same pendent group. Use of the controlled polymerisation techniques allows the length of the synthesised polyvalent macromolecule to be controlled, thereby leading to the preparation of polyvalent macromolecules with narrow molecular weight distributions.

As noted above, the pendent groups attached to the polymer may be different e.g. some containing SSGs, while others contain chromophores, in any desired ratio. Preferably the ratio of these groups on the polymer is less than 100:1, 10:1, around 1:1, 1:10, 1:100.

Advantageously, it is possible to influence many properties of the polyvalent macromolecule, including stability, solubility, SERRS-activity, and surface-activity, through control of the chemical composition (e.g. by co-polymerisation or polymer modification), molar mass, molar mass distribution and chemical topography (e.g., linear, branched, hyperbranched, dendritic) of the polymer backbone. In other words, the properties of the polymer may be tuned to suit the intended application.

In some embodiments, the polymer backbone preferably comprises a co-polymer of styrene and maleic anhydride, poly(styrene-co-maleic anhydride) (PSMA). Many such polymers are commercially available and these may be easily converted into the polyvalent macromolecules of the invention by introduction of pendent groups, via standard synthetic chemistry techniques.

Preferably the polymer contains functional groups which allow for the facile introduction of other chemical species. These may be provided by any known functional or reactive group, such as anhydride, alcohol, ester, amine, acid chloride, isocyanate, alkyl halide, aromatic, thiol and carboxylic acid groups. These groups may form part of the polymer chain itself or may be present in side chains.

Chromophore

The polyvalent macromolecules of the invention may be used to bring even chromophores that have little or no affinity for the surface into close contact with the surface, by virtue of the surface-seeking groups present, and irrespective of whether the surface-seeking groups and chromophores are present on the same or different pendent groups.

As used herein, the term 'chromophore' refers to a species which is readily detectable by a spectroscopic method including, but not limited to fluorescence spectroscopy, infrared spectroscopy, UV/vis spectroscopy, plasmon resonance emission and absorption, Raman spectroscopy, surface enhanced Raman spectroscopy (SERS), surface enhanced resonance Raman spectroscopy (SERRS), and Coherent Antistokes Raman Scattering (CARS).

In some contexts, a species containing a chromophore may also be referred to as a dye.

Preferably the chromophore is detectable by fluorescence, UV, circular dichroism linear dichroism, or Raman methods such as SER(R)S, Raman Optical Activity or CARS.

Most preferably the chromophore is a SERRS-active chromophore. SERRS active chromophores are known in the art and examples include, but are not limited to fluorescein dyes, such as 5- (and 6-) carboxy-4',5'dichloro-2',7'-dimethoxy fluorescein, 5-carboxy2',4',5',7'-tetrachlorofluorescein and 5carboxyfluorescein; rhodamine dyes such as 5- (and 6-) carboxy rhodamine, 6-carboxytetramethyl rhodamine and 6-carboxyrhodamine X; phthalocyanines such as methyl, nitrosyl, sulphonyl and amino phthalocyanines; azo dyes such as those listed in C H Munro et al, *Analyst,* 1995, 120, 993; azomethines; cyanines and xanthines such as the methyl, nitro, sulphano and amino derivatives; and succinylfluoresceins.

Most preferably, the chromophore comprises an azo group (—N=N—). Preferably the azo group is conjugated, for example by bonding to at least one aromatic group such as a phenylene group. Other preferred chromophores include xanthine dyes, cyanine dyes, and squaraine dyes.

Polyvalent macromolecules of the invention may have multiple pendent groups comprising different surface-seeking groups and/or chromophores the presence of which can be detected and distinguished spectroscopically even when they are present together in a single solution or sample. These may be used in multiplexing analysis and coding techniques.

Surface-seeking-group

In this context, the term 'surface-seeking group' (or 'SSG') means a group capable of binding to a metal surface. The SSG preferentially adsorbs onto the surface through a specific interaction or interactions. These interactions may include covalent bonds, co-ordination, hydrophobic and electrostatic interactions. SSGs may be referred to as 'chemisorptive groups' as they are capable of chemisorption to the surface.

Thus SSG's are ligands which form a strong attachment to the surface preferably through the formation of one or more of any of covalent, coordinate or polar bonds. This interaction will significantly increase the thermodynamic stability of the ligand-surface system. One preferred form of such ligands is that they form more than one bond with the surface thus creating clusters or polymers involving some or all of the species present on the original surface and so further increasing the system stability.

Preferably, an SSG once attached to the surface will retain the properties of the modified surface (e.g. surface enhancement of RRS) in environments encountered by the surface in reasonable use. These could include retaining over 90% of the surface property on exposure to air or immersion in standard biological fluids such as plasma and serum, or fluids such as laboratory solvents, saline and buffer. Typically the minimum time such protection will be retained for at least 15 minutes, but preferably much longer. Polymer SSG's by virtue of the multiple attachment groups per molecule (and the ability to provide the protection of the polymer coating) generally outperform similar monomeric SSG's. Examples which are effective after months of immersion have been synthesised by the present inventors.

In the light of the disclosure herein, the skilled person will appreciate that the choice of the SSG will depend on the nature of the surface (e.g. its charge and the presence or absence of an oxide or other layer) and of any surface coatings or other species (such as citrate reducing agents) associated with it.

SSGs will generally be either complexing or chelating in nature, or will comprise bridging ligands.

For most useful surfaces, the functional group preferably comprises a Lewis base. A Lewis base has a pair of electrons which can be donated to the metal, forming a coordinative bond. Ideally, the Lewis base is actively attracted to the surface in use. Examples of functional groups ('ligands') known to complex to metals by electron donation are well known in the art, for example as described in, for example, "Advanced Inorganic Chemistry" by Greenwood and Earnshaw (Butterworth-Heinemann).

Thus suitable surface-seeking groups by which the macromolecule may be bound to the metal surface include complexing groups such as nitrogen, oxygen, sulphur and phosphorous donors; chelating groups; bridging ligands.

The triazole group (1) is rich in nitrogen lone pairs and seems to have a particular affinity for certain metal colloids. Thus, in certain embodiments of the invention, this surface-seeking group is particularly preferred. More preferably the surface-seeking group contains the benzotriazole group (2), particularly when the metal surface is silver- or copper-based, which has a high degree of conjugation (especially when deprotonated) and is thus particularly amenable to detection by techniques including SE(R)RS, which rely on label resonance.

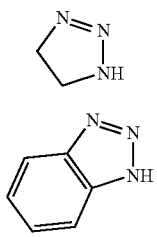

Other suitable chemisorptive functional groups include the calixarenes and the mercaptobenzotriazoles.

In other embodiments, the surface seeking group may preferably comprise polyphosphates, especially in cases where the metal surface is iron or aluminium. For gold surfaces phosphorus and sulphur containing groups may be particularly preferred (Bethell & Schiffin, Nature, 1996, 382, 581). Other preferred groups include polyhydroxides for hard metals and selenium compounds for soft metals.

Linkers

In preferred embodiments of the invention, the linker is attached between the polymer backbone and the chromophore and the surface-seeking group (which may be attached to the chromophore, or present on a different pendent group).

However, in alternative embodiments the linker is attached between the surface-seeking group and the polymer backbone. The chromophore may then, optionally, not be present, or it may be attached to the surface-seeking group.

The 'linker' may be any chemical species which tethers the pendent group to the polymer backbone, for example a di-valent or multi-valent chemical species. The tether may be via covalent or non-covalent bonding, and the linker may optionally be substituted and include further functional groups. Preferably the pendent groups are attached to the polymer backbone by covalent bonds (e.g. an alkyl linker).

Alternatively the pendent groups may be attached to the polymer backbone via non-covalent bonds, such as hydrogen bonds, electrostatic interactions or van der Waals' forces. For example a biopolymer such as streptavidin is capable of forming very strong non-covalent bonds with biotin-based systems, and either of these may be functionised with dyes, surface seeking groups or dyes with surface seeking groups to then generate the polymeric species. Other non-covalent linkers include nucleic acids which are functionlised on one strand to contain surface seeking groups and a complementary strand with dyes so that when they hydrogen bond to form the polymeric species.

Pendent Group

In some embodiments of the macromolecules of the invention, preferred pendent groups may be represented by formula 3, below:

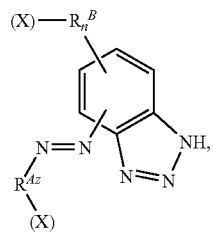

wherein $R^{Az}$ is an azo substituent, as defined below, each $R^B$ is independently a benzo substituent, as defined below, and n is 0, 1, 2 or 3; and wherein one of $R^B$ or $R^{Az}$ is bonded to X, where X is the linker.

In the above formula 3, it can be seen that the —N═N—$R^{Az}$ group represents the chromophore and the benzotriazole group (optionally substituted by $R^B$) represents the surface-seeking group.

As previously discussed, it is preferred that the linker X is attached between the polymer backbone and the chromophore, i.e. via the azo substituent $R^{Az}$ in Formula 3.

In some embodiments, it is preferred that the pendent group is selected from the group consisting of formulae 3A-3D:

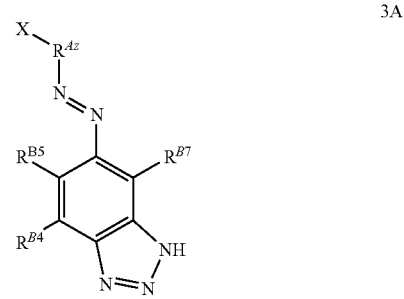

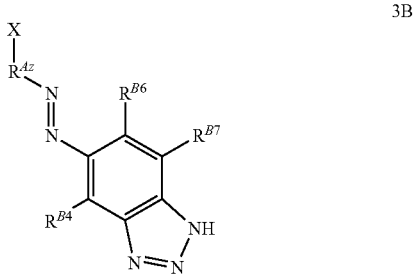

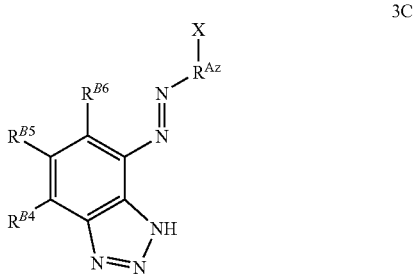

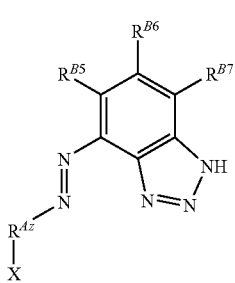

wherein $R^{Az}$ is an azo substituent, each of $R^{B4}$, $R^{B5}$, $R^{B6}$ and $R^{B7}$ is independently H or a benzo substituent, and X is a linker as previously defined.

In certain preferred embodiments, the pendent group is a compound of formula 3B above.

The azo substituent $R^{Az}$:

$R^{Az}$ may be selected from $C_{5-20}$ aryl and is optionally further substituted.

In some preferred embodiments, $R^{Az}$ is selected from monocyclic $C_6$ carboaryl or $C_{5-7}$ heteroaryl, and is optionally further substituted.

In other embodiments, $R^{Az}$, is preferably selected from bicyclic $C_{9-10}$ carboaryl or $C_{8-14}$ heteroaryl, and is optionally further substituted. More preferably, $R^{Az}$, is selected from bicyclic $C_{10}$ carboaryl or $C_{9-10}$ heteroaryl.

In some preferred embodiments, $R^{Az}$, is a group of the formula:

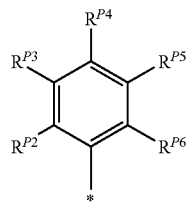

wherein each of $R^{P2}$, $R^{P3}$, $R^{P4}$, $R^{P5}$ and $R^{P6}$ is independently selected from:

the linker X, —H, -halo, $C_{1-7}$ alkyl, $C_{3-10}$ cycloalkyl, $C_{5-20}$ aryl, —C(O)R, —CO$_2$H, —C(O)NR$_2$, —OR, —NR$_2$, —N$_3$, —NO, —NO$_2$, —CN, —CH=NR, —C=N(OH)R, —NHC(=O)NHR, —NHC(=S)NHR, —NHC(=O)R, —OP(=O)(OR)$_2$, —SiR$_3$, —SR, —SSR, —SO$_3$H, —SeR, —SnR$_3$, and —PbR$_3$, wherein each R is independently H, $C_{1-7}$ alkyl, $C_{3-10}$ cycloalkyl or $C_{5-20}$ aryl;

or two adjacent groups selected from $R^{P2}$, $R^{P3}$, $R^{P4}$, $R^{P5}$ and $R^{P6}$, together with the atoms to which they are attached, form a fused $C_{5-6}$ aryl ring, which may optionally be substituted; and the remaining groups from $R^{P2}$, $R^{P3}$, $R^{P4}$, $R^{P5}$ and $R^{P6}$ are as previously defined.

In certain embodiments, it is preferred that $R^{P2}$ and $R^{P3}$ form a fused benzene ring. In other preferred embodiments $R^{P3}$ and $R^{P4}$ form a fused benzene ring. The other substituents are preferably selected from —H, —OR, —NR$_2$, $C_{1-4}$ alkylamino, —NO$_2$ and —CN, where each R is as previously defined.

In other embodiments it may be preferred that no fused ring is formed.

It is preferred that one of $R^{P2}$, $R^{P3}$, $R^{P4}$, $R^{P5}$ and $R^{P6}$ is the linker X. Most preferably $R^{P4}$ is X.

The benzo substituents, $R^B$ $R^{B4}$, $R^{B5}$, $R^{B6}$ and $R^{B7}$ are independently selected from: the linker X, —H, -halo, $C_{1-7}$ alkyl, $C_{3-10}$ cycloalkyl, $C_{5-20}$ aryl, —C(O)R, —CO$_2$H, —C(O)NR$_2$, —OR, —NR$_2$, —N$_3$, —NO, —NO$_2$, —CN, —CH=NR, —C=N(OH)R, —NHC(=O)NHR, —NHC(=S)NHR, —NHC(=O)R, —OP(=O)(OR)$_2$, —SiR$_3$, —SR, —SSR, —SO$_3$H, —SeR, —SnR$_3$, and —PbR$_3$, wherein each R is independently —H, $C_{1-7}$ alkyl, $C_{3-10}$ cycloalkyl or $C_{5-20}$ aryl;

Preferably the pendent group is of Formula 3B, above, and $R^{B4}$, $R^{B6}$ and $R^{B7}$ are independently selected from H, NR$_2$, where each R is as previously defined, or a maleimido group. If $R^{B4}$, $R^{B6}$ or $R^{B7}$ are NR$_2$, preferably R is H. Most preferably $R^{B4}$, $R^{B6}$ and $R^{B7}$ are all H.

The Linker X

Preferably X is selected from the group consisting of $C_{1-10}$ alkylene, $C_{5-20}$ arylene, and -A-(CH$_2$)$_n$—B—, where A and B are each independently selected from: a direct bond, CH$_2$, O, S, NR, where n is an integer from 0 to 5 and R represents H or $C_{1-5}$ alkyl.

Most preferably the linker is selected from —NH—(CH$_2$)$_n$—NH— where n is from 1 to 5. The linker may be attached to the polymer backbone via e.g. an amide bond (—C(O)—NH—) formed between an amino group of the linker and a carbonyl group on the backbone. Other types of covalent bond involving the amino group of this preferred linker are also possible, and are known in the art.

A particularly preferred pendent group is a group of formula 3B-i:

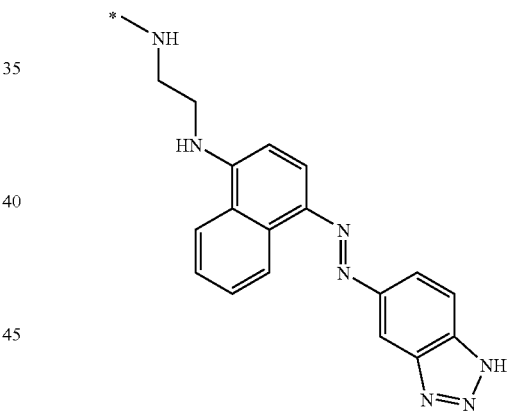

Synthesis

The invention further provides processes for producing polyvalent macromolecules as described above, which processes comprises (a) providing a synthetic polymer backbone and (b) attaching pendent groups to functional groups on said polymer backbone, wherein some or all of said pendent groups comprise: (i) a linker, which is or becomes bound to the polymer backbone; (ii) a surface-seeking group, which is capable of binding to a metal surface; and (iii) optionally a chromophore, which is detectable by at least one spectroscopic method.

In another embodiment the invention provides processes for producing polyvalent macromolecules as described above, which process comprises (a) providing a polymer backbone and (b) attaching pendent groups to said polymer backbone, wherein each pendent group comprises: (i) a linker, which is or becomes bound to the polymer backbone; (ii) a surface-seeking group, which is capable of binding to a metal surface; and (iii) a chromophore, which is detectable by at least one spectroscopic method. Optionally a biomolecule is subsequently attached to said polymer.

In another embodiment the invention provides processes for producing polyvalent macromolecules as described above, which process comprises (A) providing a polyvalent macromolecule comprising: (a) a synthetic polymer backbone and (b) pendent groups attached to said polymer backbone, wherein some or all of said pendent groups comprise: (i) optionally a linker, (ii) a surface-seeking group, which is capable of binding to a metal surface, (B) attaching a chromophore to said polyvalent macomolecule, optionally via a linker.

In certain preferred embodiments, the polyvalent macromolecules of the present invention may advantageously be prepared from a conventional, preferably commercially available, polymer, by reaction with a pendent group precursor. For example, a precursor (4) to preferred pendent group 3, above, may be prepared using standard chemistry from 5-aminobenzotriazole and N-(1-naphthyl)-ethylenediamine (D. Graham et al, *Chem. Commun.*, 2001, 11, 1002). This type of precursor may then be tethered to a polymer backbone via the primary amine group. For example, multiple copies of ABTNEDA may be introduced into the side-chains of the preferred commercially available synthetic copolymers of styrene and maleic anhydride, by reaction with the anhydride groups in the backbone (as shown in FIG. 1).

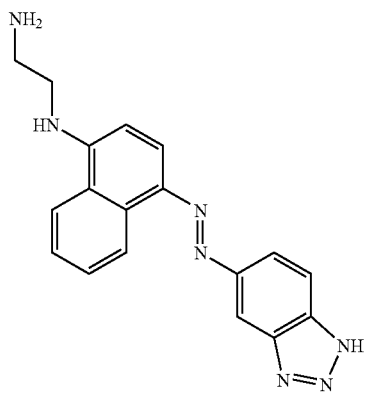

4

N-[4-(5'-azobenzotriazolyl)naphthalen-1-yl)ethylene diamine (ABTNEDA)

In another embodiment the invention provides processes for producing polyvalent macromolecules as described above, which process comprises (a) providing synthetic monomers, wherein some or all of said monomers (e.g. greater than or equal to 10, 20, 30, 40, 50%) comprise a pendent group, wherein some or all of said pendent groups comprise: (i) optionally a linker; (ii) a surface-seeking group, which is capable of binding to a metal surface; and (iii) optionally a chromophore, which is detectable by at least one spectroscopic method; (b) causing or allowing polymerisation of the monomers to form the polyvalent macromolecule. The monomers may be different so as to generate co-polymers—for example two 'block' species may be used, only one of which comprises the pendent group. Similarly different monomers may respectively provide chromophores and SSGs.

Different Pendent Groups

As noted above, in some embodiments, the polyvalent macromolecules of the invention may comprise more than one type of pendent group. These macromolecules may be synthesised, for example, by co-polymerisation of monomers having different pendent groups attached, or by reaction of the pre-formed polymer backbone with more than one type of precursor.

Advantageously this may enable the macromolecules to bind to more than one type of metal surface simultaneously. For example, block co-polymerisation to create a macromolecule having one part which adheres to iron (e.g. via a polyphosphate SSG) and another part which adheres to silver (e.g. via a benzotriazole SSG) would enable controlled formation of magnetic clusters which could be of use for nanoscale separation and detection. Similarly, macromolecules which contain both thiol containing SSGs and carboxylate or amine SSGs could be used to bind first silver and then gold nanoparticles (carboxylate and amines will not bind to gold), in order to alter absorption/plasmonic properties of the surfaces.

Functionalisation

It is also preferred that the polymer backbone has further functional groups which may be used to tether molecules such as target binding species to macromolecule.

In this context, the target binding species (TBS) may be any functional group, molecule or biomolecule which binds specifically to an analyte which is to be detected, and which is attached to the polyvalent macromolecule, preferably via the polymer backbone. For example in the case of DNA sequence detection, the target binding species. may be a substantially complementary DNA sequence.

Preferred molecules are biomolecules such as oligonucleotides. For example carboxylic acid groups on the polymer backbone can be coupled with a number of functionalities, in particular nucleophilic functionalities such as amines, by use of a coupling reagent, for example a diimide. Other species which may be coupled to carboxylic acid groups include without limitation alcohols, thiols, amines, and hydrazines. Alternatively, as will be readily appreciated by one skilled in the art, various other functional groups suitable for coupling to biomolecules could be present on, or could be introduced into, the polymer backbone of the macromolecule. For example nucleophilic groups (such as hydroxy or amino), and electrophilic groups such as alkyl halides, isocyanates and carbonyl derivatives including anhydrides and active esters. The coupling of the biomolecules to the polymer backbone may be done directly, or may be achieved with the use of one or more coupling reagents. For example carbodiimides (such as dicyclohexylcarbodiimide (DCC) or 1-ethyl-3-(3-dimethylaminopropyl)-carbodiimide hydrochloride (EDC.HCl)) may be used as coupling reagents for the formation of amide bonds.

A further aspect of the present invention therefore provides a polyvalent macromolecule, as described above, further comprising at least one attached biomolecule.

In this context the term 'biomolecule' refers to a biological species, whether natural or artificial, and includes proteins (including enzymes, antibodies), polypeptides, peptides, amino acids, polysaccharides, nucleic acids (including oligonucleotides, DNA, RNA, apatamers, oligonucleotide-peptide conjugates (OPCs), and modified nucleic acids such as PNA or LNA) lipids, phospholipids, glycolipids, co-factors, hormones, vitamins, neurotransmitters, and so on.

As used herein "antibody" should be construed as covering any specific binding substance having a binding domain with the required specificity. Thus, this term covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of Chimaeric antibodies are described in EP-A-0120694 and EP-A-0125023. Also covered are fragments of antibodies capable of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VI and VH domains of a single antibody; (iv) the dAb fragment (Ward, E. S. et al., Nature 341, 544-546 (1989) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P Holliger et al Proc. Natl. Acad. Sci. USA 90 6444-6448, 1993).

In some preferred embodiments, the biomolecules are antibodies. In other preferred embodiments, the biomolecules are oligonucleotides.

Preferably the biomolecules are attached to the polymer backbone. Preferably this attachment is through covalent bonds. However the biomolecule may also be attached via non-covalent interactions, for example by ionic or hydrogen-bonding, or may be attached elsewhere, such as via a pendent group.

Other species, which may also be of use as target binding groups in analytical techniques, may also be attached to the polyvalent macromolecules in the same way as described above. For example it may be desired to attach the polymers of the present invention to boronic acids, agonists, antagonists, drugs, metal complexing groups (for binding to specific metal ions), indicator dyes (such as methyl red, calcium responsive dyes), artificial molecular receptors, dendrimers, and so on.

Preferably the attached biomolecule is useful as a probe in biological assays and labelling techniques. For example, antibodies may be used to target particular cells and oligonucleotide probes may be used in assays to detect target nucleic acid sequences in a sample, as discussed in more detail below.

Metal-containing Compositions and Aggregates

Another aspect of the invention provides compositions comprising a metal providing a surface; said metal surface being coated with a polyvalent macromolecule as described above, wherein the surface-seeking groups of said polyvalent macromolecule interact with the metal, to adhere the macromolecule to the surface.

The polyvalent macromolecule may cover the surface completely, or it may only partially coat the surface.

In certain embodiments, the macromolecule adhered to the metal surface may also comprise attached biomolecules, or other species. Preferably these are attached via the polymer backbone of the macromolecule, as described above.

In certain preferred embodiments, the metal surface is the surface of a metal nanoparticle, or of a nanoparticle aggregate.

In the context of the present application, the term 'nanoparticle aggregate' refers to a group of at least two metal nanoparticles associated with one another to form a larger 'aggregate' particle.

Accordingly, a further aspect of the present invention provides a nanoparticle aggregate comprising at least two metal nanoparticles and a polyvalent macromolecule adhered-to the metal surface.

The polyvalent macromolecule is preferably a polyvalent macromolecule according to the invention, as described in detail above. The above-described definitions and preferences therefore apply equally to this aspect of the invention. The polyvalent macromolecule may also comprise biomolecules attached to the polymer backbone, as discussed above.

The nanoparticle aggregates of the invention are coated and stabilised by the polyvalent macromolecules of the invention. These polyvalent macromolecules, as described in detail above, comprise surface-seeking groups which are capable of binding to the metal surface. This enables the polyvalent macromolecule to adhere to the surface of the metal. The polyvalent macromolecules self-assemble on the metal surface. They may form a partial coating on the surface, or under certain conditions may fully coat or encapsulate the surface.

Due to the large size of the macromolecules and, preferably, the presence of multiple copies of the surface-seeking group, the macromolecule may bind to two or more nanoparticles simultaneously, thus promoting aggregate formation and stabilising said aggregates once formed. Advantageously, the aggregates may be of uniform shape and size and be stable long-term in suspension or solution.

The nanoparticle aggregates of the present invention may be formed by treatment of a suitable metal nanoparticle preparation, for example a reduced metal colloid, with the polyvalent macromolecules of the invention.

In some embodiments, the aggregates may comprise nanoparticles of more than one metal. These may be formed, for example, using polyvalent macromolecules comprising more than one type of pendent group, containing surface-seeking groups appropriate to the different metals.

To further increase the stability of the aggregates, they may be encapsulated within beads of a second polymer, such as a cross-linked polymer.

The nanoparticle aggregates of the invention may further comprise biomolecules, or other species, attached to the polymer backbone of the polyvalent macromolecules which are adhered to their surface. These may be introduced into the polyvalent macromolecules themselves, as discussed above, or in alternative embodiments they may be attached to the nanoparticle aggregates after they are formed.

Preferably the biomolecules are attached via covalent bonding. However in some embodiments, it may be preferable for the biomolecule to be attached via non-covalent interactions, for example by ionic or hydrogen-bonding.

The arrangement and the binding ability of the surface-seeking groups for metal surfaces therefore allows adsorption of biomolecules firmly onto the surface of metal nanoparticles without the need for charge reducing agents. The attachment and reporting role of the macromolecules and the sensing capability of the biomolecules remain independent.

Uses and Methods

As described above, the macromolecules and aggregates of the present invention represent a very flexible system which may be used to meet many targets.

Advantages of the polyvalent macromolecular coating on a metal surface may include:

1 Reduced corrosion of the metal surface in many environments, including biologically relevant solutions such as saline solution and buffer.
2 Incorporation within the polymer of labels, such as dye labels, which are tightly held to the surface and for which the bonding is stable with time.

3 The ability to add a number of labels in one polymer molecule, which gives good multiplexing potential and helps control the relative intensity of dye mixtures.

4 The ability to couple biomolecules to the labelled surface by standard chemistry which need not involve the labelling moiety.

Some possible applications are discussed below.

As discussed above, the polyvalent macromolecules of the present invention can induce aggregation and control the aggregation state of metal nanoparticles and stabilise the aggregated particles.

In particular, the present inventors have found that at certain concentrations, polyvalent macromolecules of the invention aggregate metal nanoparticles into controlled clusters through complexation of the surface-seeking groups to the metal surface and a stabilisation effect from a negatively charged polymer backbone. The size of the aggregates is controlled in these systems (at between 10 and 20 particles) and smaller nanoparticles (of about 20 nm diameter) seemed to be selected for the cluster formation.

Therefore, an aspect of the present invention provides a method for controlled aggregation of metal nanoparticles, comprising the step of adding a polyvalent macromolecule according to the invention to a preparation (e.g. suspension) of said nanoparticles.

The present invention further provides a method for making a metal nanoparticle using the polyvalent macromolecules described elsewhere herein. Polyvalent macromolecules may be used as templates for the template-directed synthesis of metal nanoparticles. The use of polyvalent macromolecules as templates for template directed synthesis of metal nanoparticles, allows the size and shape of the nanoparticles produced to be controlled.

Methods for preparing metal nanoparticles from polymers generally are known in the art and do not per se form part of the present invention. However the use of the polyvalent macromolecules in such methods does form an aspect of the invention.

Generally speaking, there are two approaches for preparing metal nanoparticles using polymers (this term is used generally here to relate to polymers and copolymers, including those having a complex architecture), that is by ex situ and in situ methods.

In ex situ methods metal nanoparticles are formed first and then dispersed and\or stabilised by polymers.

For in situ methods, silver nanoparticles or nanofibers are generated in the polymer matrix by chemical reduction or thermal or UV or microwave induced reduction (see e.g. Kong & Jang (2006) Chem. Commun. 3010-3012; Mallick et al. Journal of Materials Science 39 (2004) 4459-4463; Kuo & Chen, J. Phys. Chem. B 2003, 107, 11267-11272; Huang et al. Journal of Polymer Science: Part A: Polymer Chemistry, Vol. 44, 3843-3852 (2006); Wang et al. Materials Chemistry and Physics 94 (2005) 449-453; Ciefbien, New J. Chem., 1998, Pages 685-691

Preferred polymers for use in this aspect are those having carboxyl, amino, pyridyl, nitrile, hydroxyl, urethanes, thiol or thiol functional groups.

Thus an in situ method for making a metal nanoparticle may comprise the steps of . . .
(i) providing a polyvalent macromolecule as described above;
(ii) contacting this with metal ions;
(iii) reducing the metal ions to form the nanoparticle in situ.

Typically this is performed as a one-step method.

In other in situ methods, the polyvalent macromolecule is generated from monomers or oligomers, and the metal ions are reduced, in a single reaction. Thus the methods of synthesis described above may be performed in the presence of metal ions, and include a reduction step for forming the nanoparticle in situ. Typically this reduction step is performed in the context of a 'one-step' and 'one-pot' method.

An ex situ method for stabilising a metal nanoparticle may comprise the steps of:
(i) providing a polyvalent macromolecule as described above;
(ii) contacting it with the metal nanoparticle.

Anti-corrosion Agents

Corrosion is defined as damage to the metal surface resulting from chemical or electrochemical reaction with the surrounding medium. Coating of the metal surface with the polyvalent macromolecules of the invention may prevent this reaction from occurring and stabilise the metal surface.

Polyvalent macromolecules of the invention incorporating benzotriazole groups are useful anti-corrosion agents for silver. Anti-corrosion agents for other metals may also be provided, by choosing the appropriate surface-seeking groups.

Accordingly, another aspect of the present invention provides a method of reducing corrosion on a metal surface, comprising the step of contacting said metal surface with a polyvalent macromolecule, wherein the polyvalent macromolecule is as described above.

In preferred embodiments the metal surface is selected from gold, silver, copper, iron and aluminium and the polyvalent macromolecule preferably comprises a surface-seeking group appropriate to the metal. Appropriate surface-seeking groups for a particular metal will include groups known to have a binding affinity for the particular metal and will be known to those in the art. Some preferred surface-seeking groups for different metals were discussed earlier.

Breaking the bond between the metal surface and the macromolecule (due to corrosion effects, for example) will alter the optical signals from the chromophore portion of the macromolecule, including (but not exclusively) plasmon resonance, SERRS and resonance Raman scattering. Therefore, the polyvalent macromolecules of invention also provide a new indicator anti-corrosion system which is applicable to many forms of metal surface.

A further aspect provides a method for detecting corrosion of a metal surface, comprising the steps of:
(i) contacting said metal surface with a polyvalent macromolecule, wherein said polyvalent macromolecule is as described above;
(ii) analysing a signal from said polyvalent macromolecule to detect changes resulting from corrosion of the metal surface.

Analytical and Bioanalytical Methods

Protected particles with multiplex and stable labelling are a prerequisite for many nanoparticle based assays. For example the nanoparticle aggregates of the present invention could be of use in the assays similar to those suggested by the present inventors in WO 97/05280 and WO 99/60157, which utilise SERRS detection. Other assays may include those utilising detection by NMR or ESR (in each case appropriate labels can be appended to the molecules of the invention).

The nanoparticle aggregates of the present invention could also be of use in other assays. For example, the labelling of secondary antibodies for bioarray tests using nanoparticles of silver or gold treated with the polyvalent macromolecules of the invention is relatively simple. The degree of multiplexing created per single point detected optically is better using the aggregate nanoparticles of the invention than in other systems. The result is an increase in the multiplexing capacity of biodetection arrays.

The stability of the aggregate nanoparticles of the invention enables them to exist more readily in biomedia and, as such, the technique will be helpful for assays such as single pot DNA analysis.

For example, in a simple sandwich hybridisation assay, the presence of a target DNA sequence in a sample may cause capture of oligonucleotide-labelled nanoparticle aggregates according to the invention onto the surface of magnetic microbeads. Interrogation of the immobilised beads, for example with a Raman microscope, then allows detection of the capture event, which results in a change in the detected signals from the chromophore (e.g. intense SERRS signals). Such an assay is described in detail in Example 5.

Other, non-particulate, metal surfaces treated with the polyvalent macromolecules of the invention may also be of use in bio-analysis techniques, in particular in SER(R)S techniques.

For example, surfaces have been recently developed which control surface plasmons and hence govern SER(R)S amplification (e.g. Klarite®, Mesophotonics Ltd).

Accordingly, another aspect of the present invention provides the use of a metal surface, coated with a polyvalent macromolecule of the invention, in a biological assay.

Preferably the polyvalent macromolecule comprises attached biomolecules. Alternatively, if the metal surface is negatively charged, an analyte (e.g. DNA, protein or other biomolecule) which is positively charged may adhere to the surface through ionic or hydrogen bonds, enabling its detection at the surface by a technique such as SER(R)S. For example DNA could be tagged with a positively charged dye such as ruthenium tris-bipyridyl or with propargyl amines (see for example WO 97/05280). Advantageously, if a chromophore is present in the polyvalent macromolecule which is adhered to the surface, as well as attached to the analyte, this may be of use for signal calibration purposes.

Preferably the biological assay is one which involves the use of SERRS detection. More preferably the assay is for the detection of nucleic acids and/or the identification of nucleic acid sequences, such as the assays described in WO 97/05280, WO 99/60157 and WO 2005/019812.

Preferably the assay comprises the steps of:
(i) providing a metal surface coated with a polyvalent macromolecule according to the invention, wherein said polyvalent macromolecule comprises a target binding species;
(ii) measuring spectroscopic signals from said polyvalent macromolecule;
(iii) exposing the metal surface to an analytical sample;
(iv) detecting the presence or absence of a target molecule in the sample by
comparing spectroscopic signals from the polyvalent macromolecule before and after exposure to the sample Preferably, the metal surface is provided by a nanoparticle aggregate of the invention.

Nanoparticles labelled with the polyvalent macromolecules of the invention, and to which specific antibodies have been attached covalently, may also be of value for biological cell stains. For example, the polyvalent macromolecules can be used to attach an antibody, protein or aptamer to a metal nanoparticle surface. Such derivatised antibodies may provide robust, tagged, nanoparticle sensors and (for example) may be used to target a cell membrane recognition in a manner which is stable in biological media. The position of the antibody could then be established by plasmon resonance. Where several different antibodies are used on one cell, each particular antibody may be recognised and distinguished by SERRS from the dyes encoded in the polymer. A similar system may be provided with the so-called 'popcorn' clusters described below, to provide sensitivity and multiplexing advantages while controlling clustering.

Polyvalent macromolecules of the invention having multiple pendent groups comprising different surface-seeking groups and/or chromophores may be used in coding techniques. By coding several macromolecules with unique combinations of pendent groups, and putting each one on each of a number of biomolecules (e.g. antibodies) each may then be recognised on a metal surface. A sandwich capture assay may then be carried out in which a capture antibody is marked with a fluorophore. Enhanced fluorescence may then be observed due to spacing of the capture antibody from the surface. The flexibility of attachment of the chromophore labels, surface-seeking groups and biomolecules to the polymer backbone of the polyvalent macromolecules allows for very versatile and extensive coding chemistry.

Definitions and Embodiments of Chemical Groups

Alkyl: The term "$C_{1-10}$ alkyl", as used herein, pertains to a monovalent moiety obtained by removing a hydrogen atom from a $C_{1-10}$ hydrocarbon compound having from 1 to 10 carbon atoms, which may be aliphatic or alicyclic, or a combination thereof, and which may be saturated, partially unsaturated, or fully unsaturated.

The corresponding term "$C_{1-7}$ alkyl" pertains to a moiety so obtained from a hydrocarbon having from 1 to 7 carbon atoms, and so on.

Examples of saturated linear $C_{1-7}$ alkyl groups include, but are not limited to, methyl, ethyl, n-propyl, n-butyl, and n-pentyl (amyl).

Examples of saturated branched $C_{1-7}$ alkyl groups include, but are not limited to, iso-propyl, iso-butyl, sec-butyl, tert-butyl, and neo-pentyl.

Examples of saturated alicyclic $C_{1-10}$ alkyl groups (also referred to as "$C_{3-10}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of unsaturated $C_{1-7}$ alkyl groups which have one or more carbon-carbon double bonds (also referred to as "$C_{2-7}$ alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-10}$ alkyl groups which have one or more carbon-carbon double bonds (also referred to as "$C_{3-10}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

Aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups", in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), naphthacene ($C_{18}$), and pyrene ($C_{16}$).

Examples of aryl groups which comprise fused rings, one of which is not an aromatic ring, include, but are not limited to, groups derived from indene and fluorene.

Alternatively, the ring atoms may include one or more heteroatoms, including but not limited to oxygen, nitrogen, and sulphur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

Examples of $C_{5-20}$ heteroaryl groups which comprise fused rings, include, but are not limited to, $C_9$ heterocyclic groups derived from benzofuran, isobenzofuran, indole, isoindole, purine (e.g., adenine, guanine), benzothiophene, benzimidazole; $C_{10}$ heterocyclic groups derived from quinoline, isoquinoline, benzodiazine, pyridopyridine, quinoxaline; $C_{13}$ heterocyclic groups derived from carbazole, dibenzothiophene, dibenzofuran; $C_{14}$ heterocyclic groups derived from acridine, xanthene, phenoxathiin, phenazine, phenoxazine, phenothiazine.

Alkylene: The term "$C_{1-5}$ alkylene", as used herein, pertains to a bidentate moiety obtained by removing two hydrogen atoms, either both from the same carbon atom, or one from each of two different carbon atoms, of an aliphatic linear hydrocarbon compound having from 1 to 5 carbon atoms (unless otherwise specified), which may be saturated, partially unsaturated, or fully unsaturated. Thus, the term "alkylene" includes the subclasses alkenylene, alkynylene, etc., discussed below.

Examples of saturated $C_{1-5}$ alkylene groups include, but are not limited to, —(CH$_2$)$_n$— where n is an integer from 1 to 5, for example, —CH$_2$— (methylene), —CH$_2$CH$_2$— (ethylene), —CH$_2$CH$_2$CH$_2$— (propylene), and —CH$_2$CH$_2$CH$_2$CH$_2$— (butylene).

Examples of partially unsaturated $C_{1-5}$ alkylene groups include, but are not limited to, —CH=CH— (vinylene), —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH— and —CH=CH—CH=CH—CH$_2$—.

Arylene: The term "$C_{5-20}$ arylene", as used herein, pertains to a bidentate moiety obtained by removing two hydrogen atoms from each of two different ring carbon atoms of a compound having one ring, or two or more rings (e.g., fused), and having from 5 to 20 ring atoms, and wherein at least one of said ring(s) is an aromatic ring. Preferably, each ring has from 5 to 7 ring atoms. The ring atoms may be all carbon atoms ('carboarylene'), or may comprise one or more heteroatoms ('heteroarylene'). Examples of $C_{5-20}$ arylene groups include, but are not limited to phenylene, naphthylene.

The above $C_{1-10}$ alkyl, $C_{1-5}$ alkylene, $C_{5-20}$ aryl and $C_{5-10}$ arylene groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam (2-pyrrolidone), δ-valerolactam, and ε-caprolactam.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester. substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —$NR^1C(=O)R^2$, wherein $R^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and $R^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —$NHC(=O)CH_3$, —$NHC(=O)CH_2CH_3$, and —$NHC(=O)Ph$.

Acylureido: —$N(R^1)C(O)NR^2C(O)R^3$ wherein $R^1$ and $R^2$ are independently ureido substituents, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. $R^3$ is an acyl group as defined for acyl groups. Examples of acylureido groups include, but are not limited to, —NHCONHC(O)H, —NHCONMeC(O)H, —NHCONEtC(O)H, —NHCQNMeC(O)Me, —NHCONEtC(O)Et, —NMeCONHC(O)Et, —NMeCONHC(O)Me, —NMeCONHC(O)Et, —NMeCONMeC(O)Me, —NMeCONEtC(O)Et, and —NMeCONHC(O)Ph.

Carbamate: —$NR^1$—C(O)—$OR^2$ wherein $R^1$ is an amino substituent as defined for amino groups and $R^2$ is an ester group as defined for ester groups. Examples of carbamate groups include, but are not limited to, —NH—C(O)—O-Me, —NMe-C(O)—O-Me, —NH—C(O)—O-Et, —NMe-C(O)—O-t-butyl, and —NH—C(O)—O-Ph.

Thioamido (thiocarbamyl): —$C(=S)NR^1R^2$, wherein $R^1$ and $R^2$ are independently amino substituents, as defined for amino groups. Examples of amido groups include, but are not limited to, —$C(=S)NH_2$, —$C(=S)NHCH_3$, —$C(=S)N(CH_3)_2$, and —$C(=S)NHCH_2CH_3$.

Tetrazolyl: a five membered aromatic ring having four nitrogen atoms and one carbon atom,

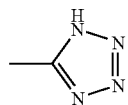

Amino: —$NR^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{1-4}$ alkyl group (also referred to as $C_{1-4}$ alkylamino or di-$C_{1-4}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —$NHCH_3$, —$NHC(CH_3)_2$, —$N(CH_3)_2$, —$N(CH_2CH_3)_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group.

Amidine: —$C(=NR)NR_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. An example of an amidine group is —$C(=NH)NH_2$.

Carbazoyl (hydrazinocarbonyl): —C(O)—NN—$R^1$ wherein $R^1$ is an amino substituent as defined for amino groups. Examples of azino groups include, but are not limited to, —C(O)—NN—H, —C(O)—NN-Me, —C(O)—NN-Et, —C(O)—NN-Ph, and —C(O)—NN—$CH_2$-Ph.

Nitro: —$NO_2$.
Nitroso: —NO.
Azido: —$N_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —$SCH_3$ and —$SCH_2CH_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —$SSCH_3$ and —$SSCH_2CH_3$.

Sulfone (sulfonyl): —$S(=O)_2R$, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —$S(=O)_2CH_3$ (methanesulfonyl, mesyl), —$S(=O)_2CF_3$ (triflyl), —$S(=O)_2CH_2CH_3$, —$S(=O)_2C_4F_9$ (nonaflyl), —$S(=O)_2CH_2CF_3$ (tresyl), —$S(=O)_2Ph$ (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —$S(=O)CH_3$ and —$S(=O)CH_2CH_3$.

Sulfonyloxy: —$OS(=O)_2R$, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —$OS(=O)_2CH_3$ and —$OS(=O)_2CH_2CH_3$.

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —$OS(=O)CH_3$ and —$OS(=O)CH_2CH_3$.

Sulfamino: —$NR^1S(=O)_2OH$, wherein $R^1$ is an amino substituent, as defined for amino groups. Examples of sulfamino groups include, but are not limited to, —$NHS(=O)_2OH$ and —$N(CH_3)S(=O)_2OH$.

Sulfinamino: —$NR^1S(=O)R$, wherein $R^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —$NHS(=O)CH_3$ and —$N(CH_3)S(=O)C_6H_5$.

Sulfamyl: —$S(=O)NR^1R^2$, wherein $R^1$ and $R^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$. A special class of sulfonamino groups are those derived from sultams—in these groups one of R$^1$ and R is a C$_{5-20}$ aryl group, preferably phenyl, whilst the other of R$^1$ and R is a bidentate group which links to the C$_{5-20}$ aryl group, such as a bidentate group derived from a C$_{1-7}$ alkyl group.

Phosphoramidite: —OP(OR$^1$)—NR$^2_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

In many cases, substituents may themselves be substituted. For example, a C$_{1-7}$ alkoxy group may be substituted with, for example, a C$_{1-7}$ alkyl (also referred to as a C$_{1-7}$ alkyl-C$_{1-7}$alkoxy group), for example, cyclohexylmethoxy, a C$_{3-20}$ heterocyclyl group (also referred to as a C$_{5-20}$ aryl-C$_{1-7}$ alkoxy group), for example phthalimidoethoxy, or a C$_{5-20}$ aryl group (also referred to as a C$_{5-20}$aryl-C$_{1-7}$alkoxy group), for example, benzyloxy.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

EXAMPLES

Materials and Methods
Synthesis of ABTNEDA:
N-[4-(-5'-Azobenzotriazolyl)naphthalen-1-yl)ethylene diamine (ABTNEDA) was synthesised as reported by Graham et al (*Chem. Commun.*, 2001, 11, 1002).

Synthesis of PD 1600, PD1700 and PD 1900:
PSMA1600, PSMA1700 and PSMA1900 were obtained from Aldrich.

Oligonucleotide Labelling:
Amine-modified oligonucleotides were obtained from Eurogentec, UK. 1-Ethyl-3-(3-dimethylaminopropyl)-carbodiimidehydrochloride (EDC-HCl) was obtained from Aldrich.

Colloid Preparation:
EDTA-reduced silver colloids were prepared as described by Fabrikanos et al (Naturforsch. B, 1963, 188, 612). The colloids were of acceptable standard if they showed a $\lambda_{max}$ of 400-410 nm.

SERRS Measurements:

SERRS spectra were acquired using an argon ion laser (514.5 nm) on a Renishaw InVIA Raman spectrometer. Stock solution of the dyes were prepared in DMSO at a concentration of $1 \times 10^{-3}$ M, and then diluted with water to the concentrations desired.

Example 1

Preparation of Polyvalent Macromolecules

Three chemically-distinct styrene-maleic anhydride copolymers were investigated:

PSMA1600, PSMA1700 and PSMA1900. PSMA1600 had a number average molecular weight of 1600 and a maleic anhydride content of 50% (w/w). The corresponding values for PSMA1700 and PSMA1900 were 33% (w/w) and 25% (w/w), respectively.

The starting copolymers were dissolved in dry THF at 60° C. and treated with an excess of ABTNEDA in the presence of triethylamine under an inert atmosphere. The products precipitated and were isolated by filtration, purified by solvent extraction (THF) and dried in vacuo. Yields: PD1600, 67%; PD1700, 58%; PD1900, 73%. The FTIR and $^1$H NMR spectra were in agreement with the structures anticipated.

Figure 1:
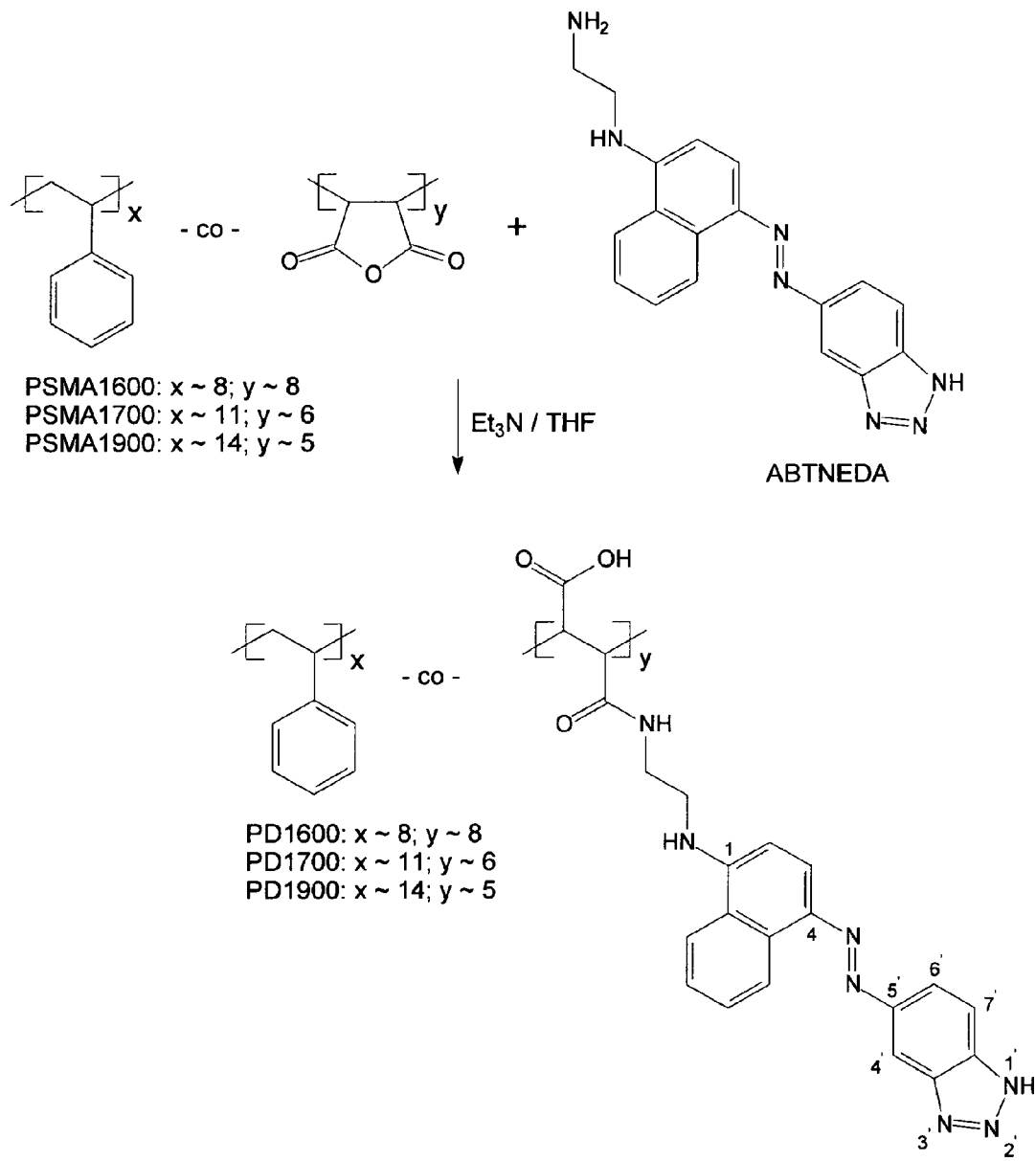
FIG. 1: Ring-opening of anhydride units in commercially-available, styrene-maleic anhydride copolymers by the azo dye ABTNEDA to give three chemically-distinct macromolecules, PD1600, PD1700 and PD1900.

Thus, three dye-containing polymers of varying molar mass and dye contents, PD1600, PD1700 and PD1900, were prepared via ring-opening of the anhydride groups present in the parent macromolecules (FIG. 1). On average, PD1600 contained eight ABTNEDA molecules per 16 monomer residues, whereas PD1700 contained six per 17 and PD1900 five per 19. The carboxylic acid groups present in the pendent amic acids of PD1600, PD1700 and PD1900 can be used for the subsequent chemical manipulation of the macromolecules, e.g., for the tethering of biomolecules (see Example 4).

Example 2

Preparation of Nanoparticle Aggregates

Figure 2:
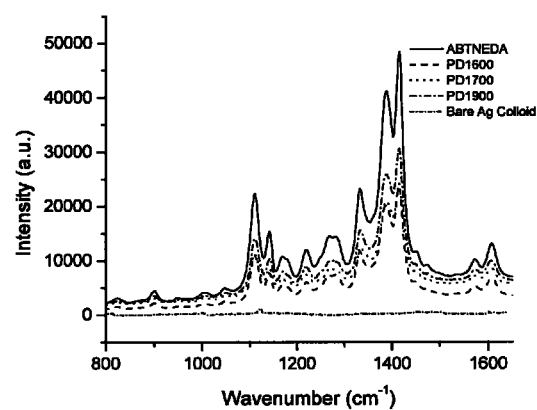
FIG. 2: SERRS spectra obtained from silver colloid loaded with the azo dye (ABTNEDA) and the three SERRS-active macromolecules, PD1600, PD1700 and PD1900. The SERRS spectrum of bare colloid (no dye present) is included for reference purposes. Dye concentrations: $2 \times 10^{-7}$ M.

To demonstrate that PD1600, PD1700 and PD1900 were potent SERRS dyes, they were incubated with silver colloid. FIG. 2 shows the SERRS spectra obtained from PD1600, PD1700 and PD1900-loaded silver colloid. In all three cases, sharp and intense SERRS signals were obtained at a dye concentration of $2 \times 10^{-7}$ M. The signals appearing at ~1395 cm$^{-1}$ can be ascribed to the azo bond. The spectrum of ABTNEDA-loaded silver colloid is also displayed in FIG. 2 (the azo band appears at ~1419 cm$^{-1}$). It is noteworthy that this spectrum is remarkably similar to the spectra of PD1600, PD1700 and PD1900, thus the tethering of ABTNEDA to the macromolecules has had minimal impact upon its spectral features. Whilst, PD1600, PD1700 and PD1900 give rise to intense SERRS spectra, it is assumed that ABTNEDA gives rise to the highest signal intensities of all because it is of low molar mass, relative to the SERRS-active macromolecules, and gives better monolayer coverage at the silver surface. In the absence of any dye (bare colloid) no signals were observed.

Example 3

Stability of Aggregates/Anti-corrosive Effects

The stability of dye-loaded, aggregated metal nanoparticles in 1.5 M aqueous sodium chloride (a powerful aggregating agent for nearly all silver colloid) was probed by electronic spectroscopy. The aim of these experiments was to test the ability of the polyvalent macromolecules to prevent hydrophilic etching of the metal surface when exposed to high salt concentrations.

Figure 3:
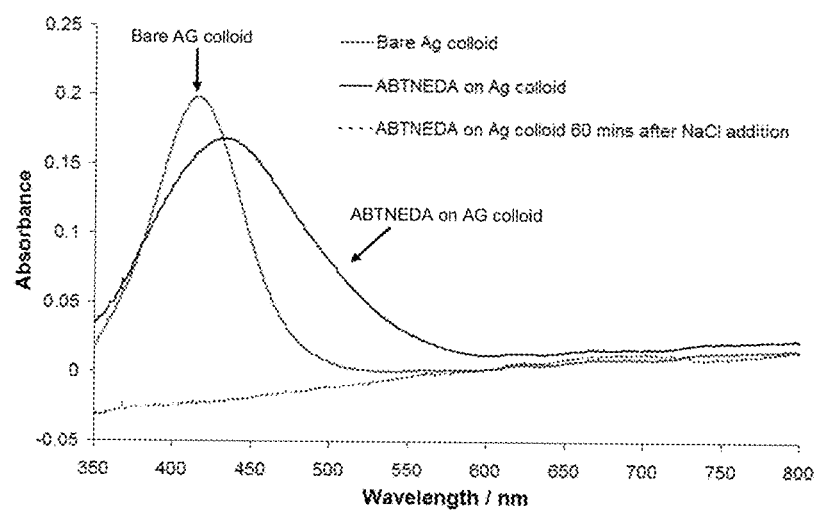
FIG. 3: Electronic spectra of ABTNEDA-loaded (a) and PD1900-loaded (b) silver colloid measured before, and 60 minutes after, exposure to 1.5 M NaCl. Dye/polymer dye concentrations: $1 \times 10^{-5}$ M.
Figure 3:
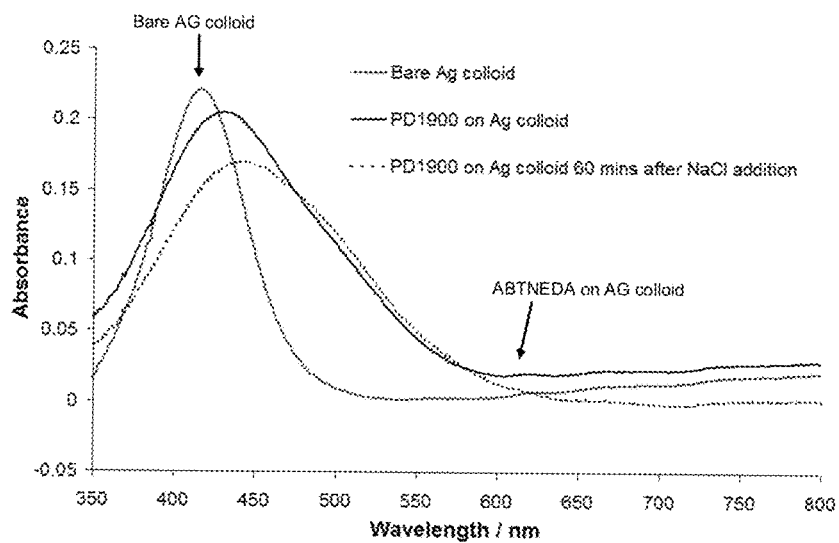
Figure 4:
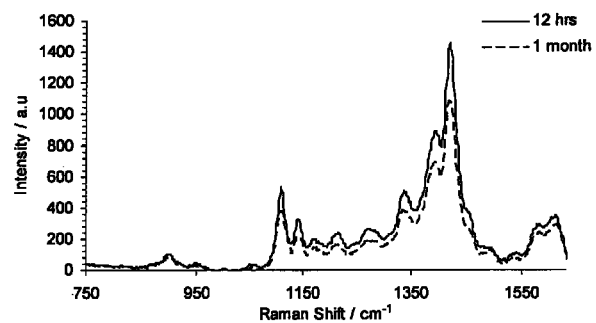
FIG. 4: SERRS spectra of PD1600-loaded silver colloid acquired after exposure to 1.5 M NaCl for 12 hours and one month. Dye concentration: $5 \times 10^{-7}$ M.

In this study, the dye concentrations were varied from $1 \times 10^{-8}$ M to $1 \times 10^{-4}$ M and the electronic spectra measured as a function of time. In addition to the three SERRS-active macromolecules, the behaviour of ABTNEDA-loaded silver colloid and silver colloid in the presence of PSMA1600, 1700 and 1900 was investigated. Silver nanoparticles of size ca. 30 nm absorb EM radiation around 400 nm, and aggregation is normally indicated by a decrease in the extinction coefficient at around 400 nm and the emergence of a new, broad absorbance band at >600 nm characteristic of the presence of larger clusters of silver colloid. PD1600, PD1700 and PD1900 were found to confer remarkable resistance onto the silver nanoparticles against NaCl-induced aggregation, provided that they were present above certain threshold concentrations (the values of which were determined experimentally: PD1600, $5 \times 10^{-7}$ M; PD1700, $1 \times 10^{-5}$ M; PD1900, $1 \times 10^{-6}$ M). At dye concentrations above the threshold concentrations, the SERRS signal intensities increased dramatically, a phenomenon which is related, presumably, to concentration-dependent control of the colloid cluster size. In contrast, ABTNEDA-loaded silver nanoparticles and silver nanoparticles in the presence of PSMA1600, 1700 or 1900, showed extremely poor resistance to NaCl-induced aggregation, irrespective of the concentration of the additive used. FIG. 3 shows the electronic spectra of ABTNEDA-loaded and PD1900-loaded silver nanoparticles measured before, and 60 minutes after, exposure to 1.5 M aqueous NaCl. FIG. 4 shows the SERRS spectrum of PD1600-loaded silver nanoparticles acquired after exposure to 1.5 M NaCl for 12 hours and one month; the two spectra are essentially identical.

These profound stabilisation effects, which have been observed in biorelevant media, may be ascribed to the polyvalent character of the macromolecules of the invention, and to the formation of monolayer/layers of the polyvalent macromolecules on the metal surface.

Example 4

Preparation of oligonucleotide-labelled Polyvalent Macromolecules

Figure 5:
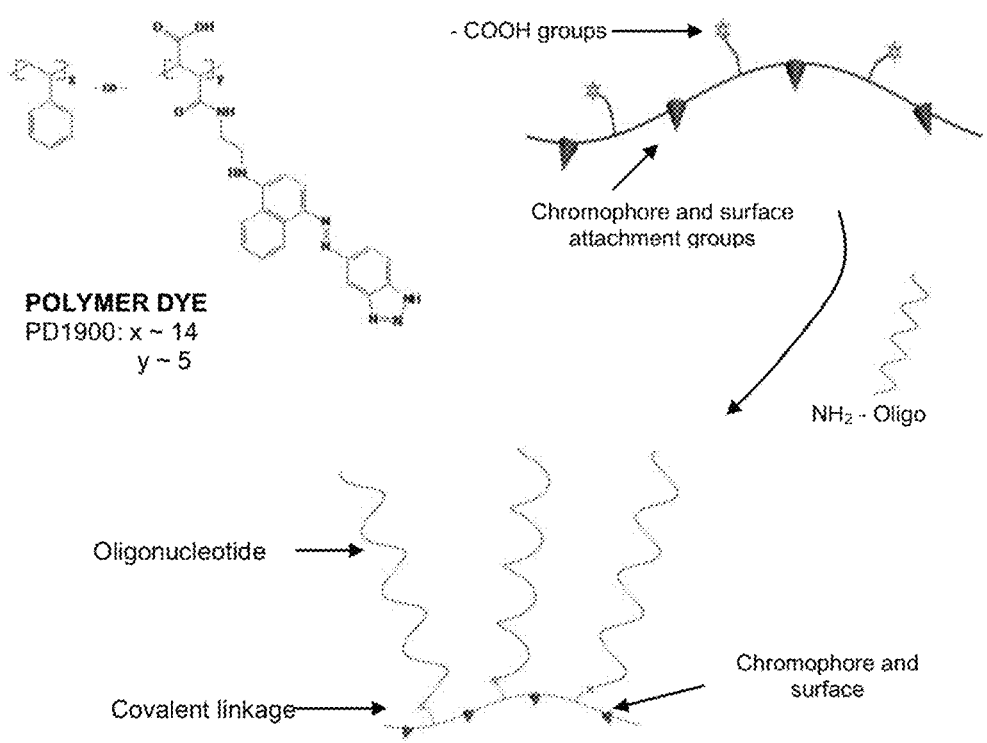
FIG. 5: Covalent attachment of oligonucleotides to polyvalent macromolecules.
Figure 6:
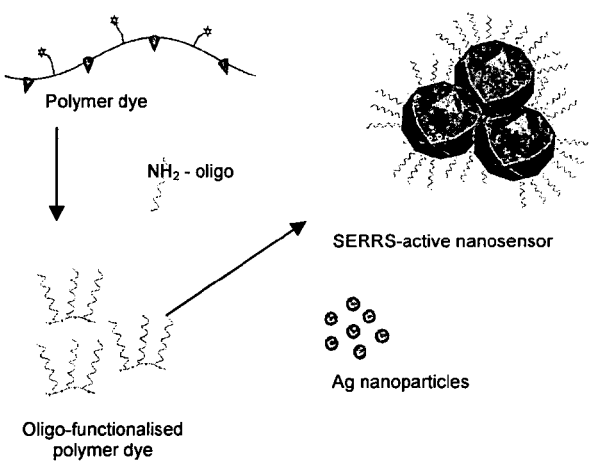
FIG. 6: Two-step conjugation method in the formation of SERRS-active oligonucleotide labelled nanoparticle aggregates.

Derivatisation of polymer dyes with oligonucleotides and their use in creating SERRS-active nanosensors is shown in FIG. 5. PD1900 was reacted with an excess of amine-modified oligonucleotide using 1-ethyl-3-(3-dimethylaminopropyl)-carbodiimidehydrochloride as an activator. Un-reacted oligonucleotide and reaction by-products were removed by centrifuging the samples, removing the supernatant and re-suspending the coloured residue repeatedly in fresh buffer followed by water. The functionalised polymer dye was then incubated with EDTA-stabilised silver colloid to produce SERRS-active nanosensors (FIG. 6).

Figure 7:
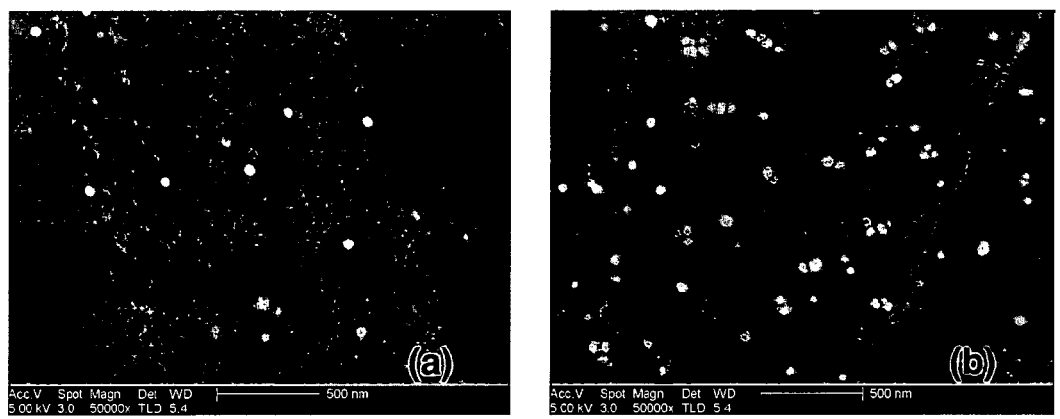
FIG. 7: SEM micrographs of silver colloid (a) and silver colloid in the presence of polyvalent macromolecule PD1900, functionalised with oligonucleotides (~$10^{-5}$ M) (b).

SEM images show that small aggregates are formed when the oligo-functionalised polymer dye is adsorbed onto silver nanoparticles (FIG. 7).

Figure 8:
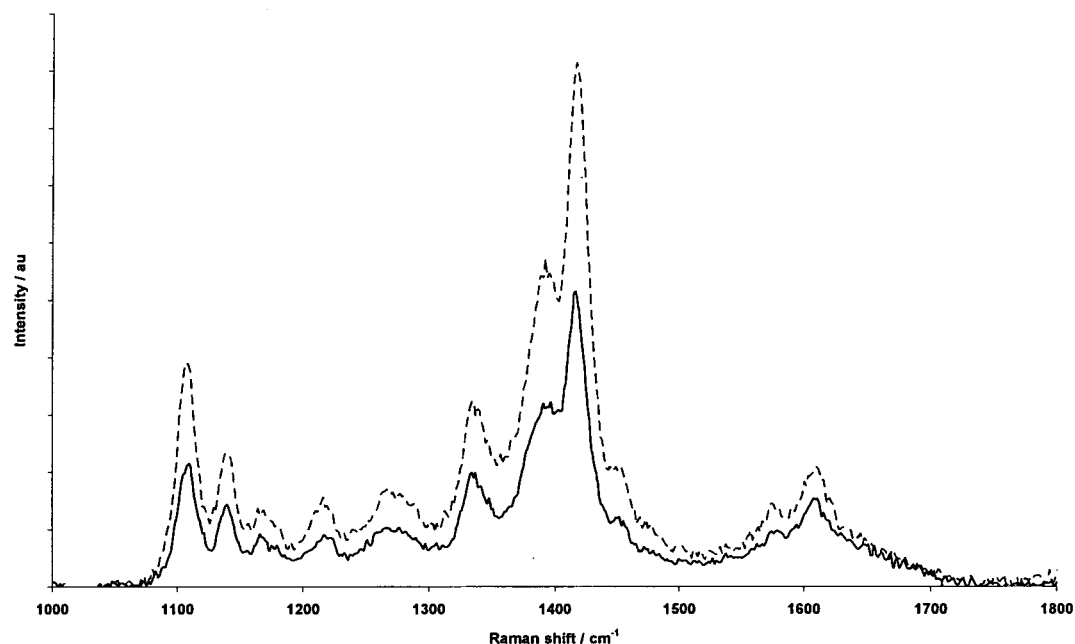
FIG. 8: SERRS spectra of $10^{-5}$M PD1900 polymer dye (dotted line) and $10^{-5}$M PD1900 functionalised with oligonucleotides

The SERRS signal remains identical to that of the parent polymer dye and is consistent with the formation of small clusters of particles at higher concentration (FIG. 8). A full spectroscopic study of a similar dye has been published (Ref: Andrikopoluos et al, *J. Mol. Struct.*, 2006, 789, 59). and from this the most intense and broad band at ~1400 cm$^{-1}$ may be assigned to a combination of azo, ring and C—N group stretches.

Example 5

Use of SERRS Nanosensors in Diagnostic Applications

Figure 9:
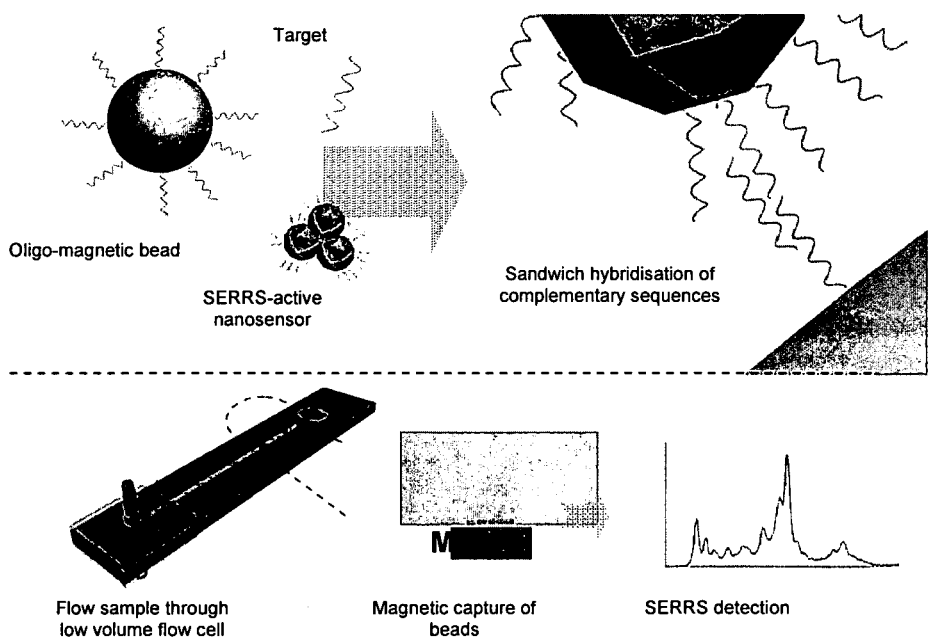
FIG. 9: Scheme of biosensor based on sandwich hybridisation of target DNA to functionalised SERRS-active nanosensors and oligo-functionalised magnetic microbeads.

To demonstrate the potential use of this material as a nanosensor for diagnostic applications, a simple assay was devised in which the SERRS-nanosensors are captured on the surface of functionalised magnetic beads (~1 μm) in the presence of a target DNA sequence (FIG. 9). This is achieved via the sandwich hybridisation of complementary strands to essentially bridge the SERRS-nanosensor and the oligo-functionalised magnetic bead. Magnetic beads are widely used in bioanalysis and their application in microfluidic devices is an area of growing interest (Ref: Gijs et al, *Microfluid Nanofluid*, 2004, 1, 22-40; Pamme, N, *Lab Chip*, 2006, 6, 24). One of the advantages of using magnetic beads is that it allows sample manipulation/concentration with the use of external magnetic fields without interfering or being in contact with the surrounding fluid, thus minimizing sample contamination. A further advantage is that a Raman microscope is used as the detection system. This allows recordal of data from a small interrogation volume, provides a high power density at the sample and scattered light is efficiently collected.

Figure 10:
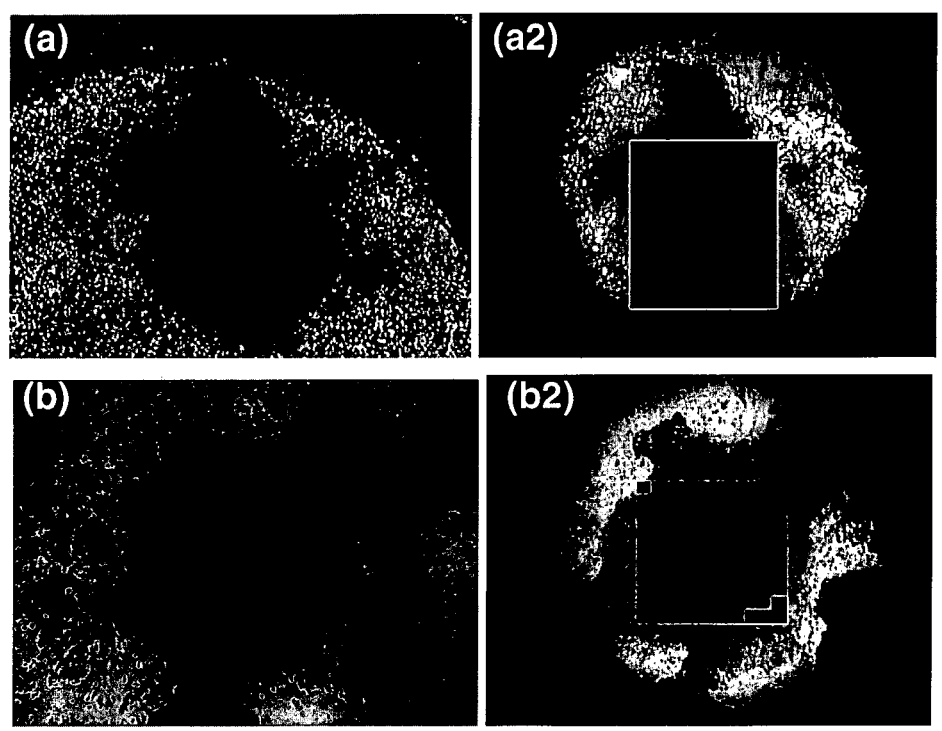
FIG. 10: Optical images of oligo-functionalised magnetic microbeads trapped in the flowcell (a & b) and corresponding, overlaid SERRS maps of a no target control (a2) and 1 nanomole of target probe (b2) assay. The intensity of each point/square relates to the relative intensity of the SERRS signal obtained at 1419 cm$^{-1}$. Black is weak and grey is intense.

SERRS-nanosensors were prepared as described earlier and these were suspended in hybridisation buffer (MgCl$_2$, KCl, Tris-HCl, pH 7) and mixed with oligo-functionalised magnetic beads and different amounts of target oligonucleotide sequence. The mixture was then heated to 90° C. for 5 minutes and cooled to room temperature over 10 minutes using the heating stage of a commercial Q-PCR instrument (Stratagene). The sample was then pumped through a low volume disposable flow cell (Aline, Inc. CA) and a single permanent magnet was positioned directly underneath the optically transparent window on the chip to trap and concentrate the magnetic beads/SERRS-nanosensor complex as it was pumped through the chip. Hybridisation buffer spiked with surfactant (Tween 20) was pumped through the microchannel to remove any un-hybridised probe/SERRS-nanosensor. The chip was mounted on the motorised x-y-z stage of a Raman microscope (Renishaw) and a low magnification objective (×10, NA 0.4) was then used to focus a green laser (514 nm, Argon ion) on the magnetically trapped beads. Mapping software (Wire 2.0, Renishaw) was then used to take multiple spectra (>100) over a defined region in 25 μm steps. This data was then used to generate a "SERRS map" based on the intensity of the most intense band at 1419 cm$^{-1}$ (corresponding to the monoazobenzotriazole dye) as shown in FIG. 10. This figure illustrates the strong difference in SERRS signal intensity when target oligonucleotide is present in the reaction mixture. Femtomole quantities of target oligonucleotide probe have been detected via this method.

Example 6

Aggregation Effects

Figure 11:
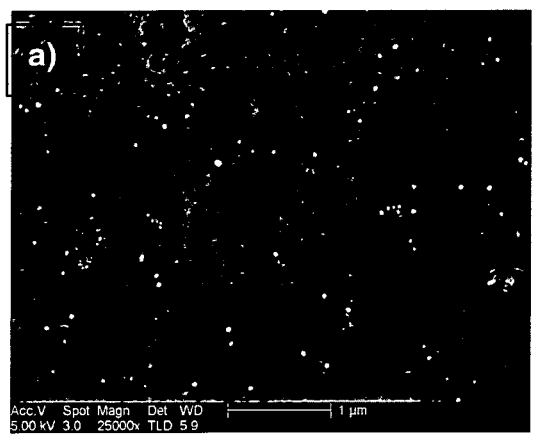
FIG. 11: Scanning electron micrographs of (a) un-modified silver nanoparticles and (b) silver nanoparticles aggregated in the presence of PD1900 ($10^{-5}$ M). Inset in (b): enlarged view of one of the clusters showing surface features. Blurring is due to particle charging under the electron beam during imaging.
Figure 11:
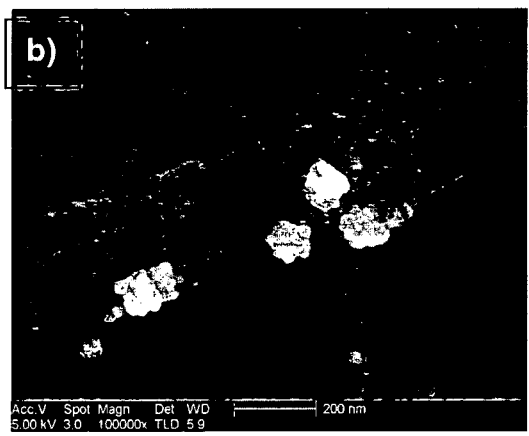

PD1900 (without attached DNA) was shown to form regular clusters (known here as popcorn or raspberries) of nanoparticles if added to colloid in higher concentrations. This does not happen if the colloid is dried out or if a monomeric SERRS dye is added. FIG. 11 shows SEM images of the silver colloid before (a) and after (b) treatment with PD1900.

Figure 12:
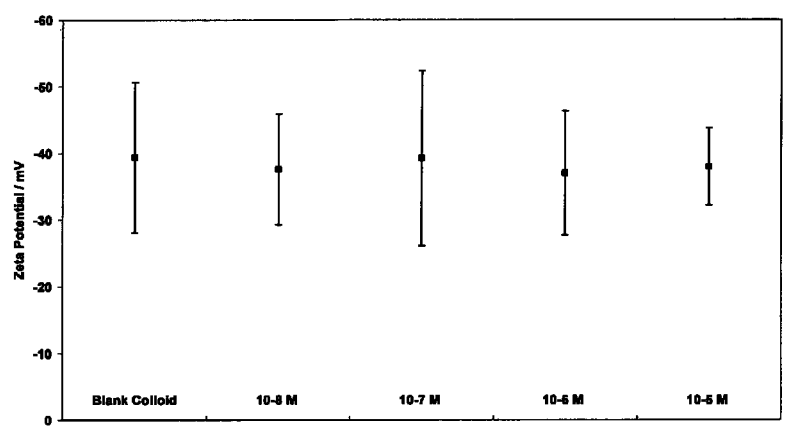
FIG. 12: ξ Potential measurements of PD1900 titrated into silver colloid.

The silver colloid used in this study was prepared in alkaline conditions in the presence of EDTA as reported by Heard and co-workers (Ref: *J. Colloid Interface Si.*, 1983, 93, 545-555) and the stability and negative charge of the particles was attributed to EDTA$^{3-}$ adsorbed at the metal-solution interface. When PD1900 was titrated into the colloidal suspension of silver nanoparticles no significant change in surface charge was observed and the results showed an overall negative charge on the particles (FIG. 12). This indicated that the displacement of surface active species by polymer dyes did not have a significant effect on the relative stability of the colloidal metal particles. The pK$_a$ of the carboxylate groups on the polymer dye chain was not determined experimentally but it may be assumed that it was approx. 4-5, as expected for a methacrylate group. This implies that the acid groups on the polymer backbone will be deprotonated at this pH, conferring an overall negative charge to the silver particles when adsorbed onto the surface.

Figure 13:
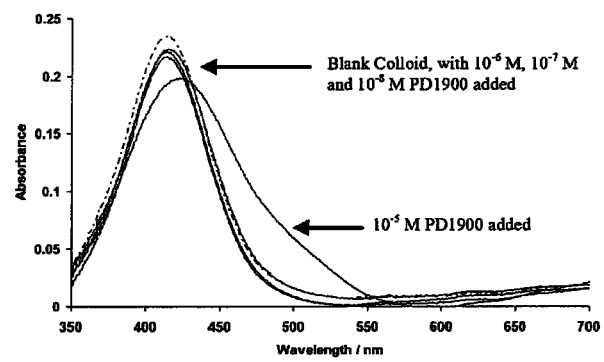
FIG. 13: Electronic absorption spectra of blank silver colloid (dotted line) and different amounts of PD1900 titrated into silver colloid (solid lines).

Electronic spectroscopy was used to study the effects of increasing polymer dye concentration in silver colloid. The frequency and shape of the main band in the UV-visible spectrum of silver colloid is indirectly related to particle size and shape through the interaction of the surface plasmon with light. The frequency of the main band can give an indication of the average particle size, the full width at half-height (FWHH) can give an indication of the particle size distribution, and aggregation is indicated by a red shift and a decrease in the extinction coefficient of the main band and the appearance of a second band at a longer wavelength. A series of solutions containing a fixed amount of silver colloid and increasing amount of polymer dye were prepared and these were left to stand at room temperature for 24 hrs prior to taking measurements (FIG. 13). Lower concentrations of polymer dye did not have a major effect on the visible absorption spectrum of the silver colloid. At the highest concentration in this study (10$^{-5}$ M) a marked shift in frequency of the main plasmon band from 412 nm to 422 nm was observed, as well as a broadening of the main band. These spectral changes suggest the formation of small aggregates in solution. However, these results differ in three key respects from those obtained with aggregating agents such as sodium chloride which are commonly used in SERRS to achieve effective enhancement. Most aggregating agents alter the surface properties to reduce charge on the particles and cause aggregation to occur. This is a dynamic process in which the formation of aggregates and the aggregate size and size distribution varies with time. Eventually the colloidal particles precipitate out. This process can be followed by following changes with time in the electronic spectrum. However, following changes in the first few hours, the general spectral properties shown in FIG. 3 remain unchanged for weeks and even months thereafter, indicating that the aggregation process has stopped. It also indicates that the aggregates are stable in suspension. In addition, aggregates of different sizes and shapes have different absorption profiles, the peaks of which are red shifted compared to the single particles. This means that there is usually a broad absorbance band towards the red. The results with 10$^{-5}$ M polymer dye added are different in that they show a definite minimum at about 600nm indicating a more defined cluster arrangement.

The size of the aggregates appears controlled at between 10 and 20 particles in a spherical spatial arrangement. In contrast, colloidal particles before treatment with dye (FIG. 11*a*) were mainly present as isolated particles with some small ill-defined clusters, probably formed on drying out the suspension. Smaller numbers of the characteristic clusters were formed at $10^{-6}$ M and no clusters were observed at lower concentrations. The aggregates are stable in suspension.

Without wishing to be bound by theory, this effect is thought to arise due to a combination of a surfactant effect, due to the carboxylates present on the polymer backbone (as these will be deprotonated and hence negative under the pH ~11 conditions used) and the ability of the benzotriazole groups on one polymer to complex to more than one particle. A similar-surfactant effect is known for other water-soluble polymers such as poly(vinyl pyrrolidone).

Figure 14:
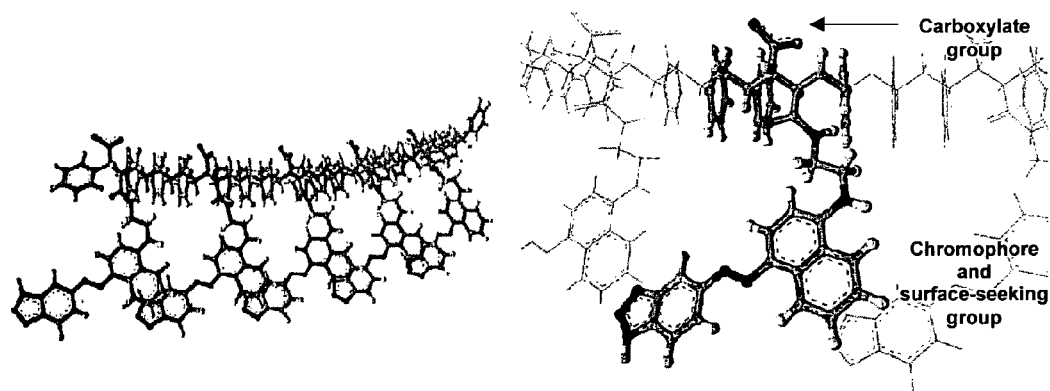
FIG. 14: Chemical structure of polyvalent macromolecule (PD1900).

FIG. 14 shows a model of a typical polyvalent macromolecule of the invention. As modelled, there are clear hydrophobic and hydrophilic sides. However, the surface seeking properties of the benzotriazole groups should direct the hydrophobic residues onto the metal surface, while the negatively charged carboxylate residues should be exposed to the surrounding environment and provide some degree of electrostatic repulsion between particles, as suggested by ξ potential measurements. This explanation would imply that, at low concentrations, the polymer dye would wrap around single particles and prevent further aggregation. Since the electronic spectrum shows some modification but suggests that single particles still dominate in the suspension, SERRS is obtained from these systems and they retain a high Zeta potential, this hypothesis appears correct. Previous studies suggest that monomeric benzotriazole dyes cover most of the available surface at concentrations of about $10^{-6}$ M. This would suggest the polyvalent macromolecule would cover the available surface between $10^{-7}$ and $10^{-6}$ M. Above this concentration range the specific aggregates form in appreciable numbers suggesting the formation of a more complex surface layer of polymer. Formation of a multilayer structure may not be sufficient to explain the clusters since each multilayer would retain the high negative charge. Without wishing to be bound by theory, it seems more likely that the dyes begin to pack in a manner that places some of the complexing groups away from the surface and in a position to bind to a second particle. Thus, particle aggregation at higher concentrations may be due to the polyvalent nature of the macromolecule, which may have the ability to complex to more than one particle providing that the distance between two particles does not exceed the length of the linear polymer.

It was noted that the particles involved in the cluster formation were typically not larger than 20 nm in size, compared to the average particle size of 40 nm. Larger particles did not seem to form clusters and remained as separate entities and occasionally as dimers and trimers as is found for untreated colloid.

Figure 15:
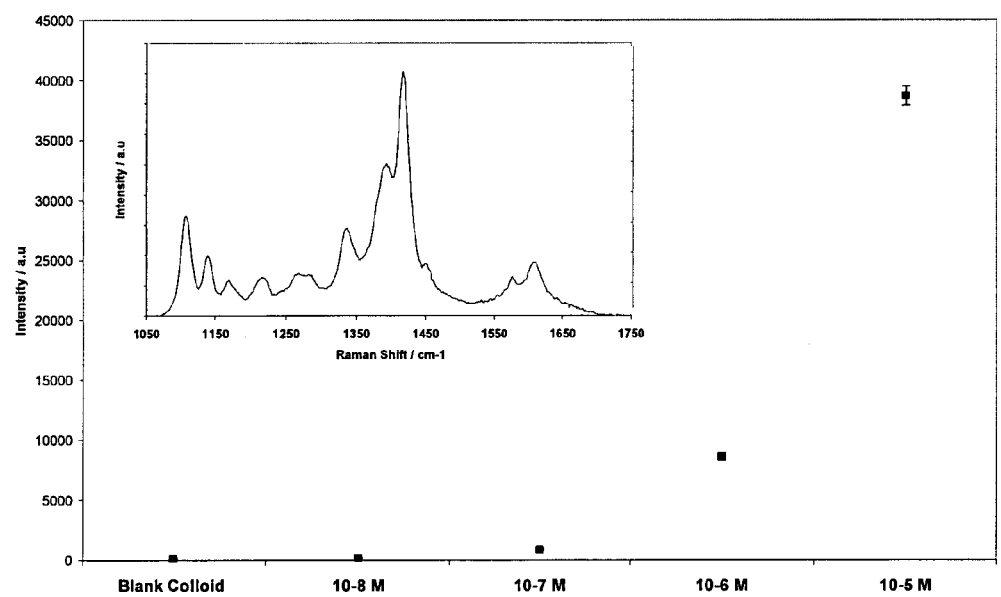
FIG. 15: Plot of SERRS intensity of the signal at 1419 cm$^{-1}$ for different concentrations of PD 1900 in Ag colloid. Each data point is the average signal of three measurements at the different concentrations. Inset: Representative SERRS spectrum of the PD1900.

Formation of controlled clusters of silver nanoparticles is of particular interest in SERRS studies. SERRS activity of colloidal dispersions with different amounts of polyvalent macromolecule, but in the absence of any other aggregating agent, was investigated. FIG. 15 shows a representative SERRS spectrum of PD1900 at $10^{-5}$ M in silver colloid and a comparison of the intensity of the main band at 1419 $cm^{-1}$ when silver colloid is treated with different amounts of PD1900. The large increase in signal intensity with increasing concentration of polymer dye may again be attributed to the formation of small clusters, since the relative SERRS activity of single particles is very low compared to dimers and larger aggregates of particles.

With DNA attached popcorn formation is largely inhibited, but small clusters of trimers and tetramers form instead. Without wishing to be bound by theory, it is proposed that the oligonucleotide-labelled macromolecule behaves as a surfactant, with hydrophilic tails due to the highly negative charge inherent to the phosphate backbone on the oligonucleotides and a hydrophobic framework based on the aromatic benzotriazole dyes and styrene moieties of the parent polymer. This arrangement and the binding ability of the benzotriazole groups for silver surfaces allows adsorption of oligonucleotides firmly onto the surface of metal nanoparticles without the need for charge reducing agents, and the attachment and reporting role of the benzotriazole dyes and the sensing capability of the oligoncleotides remain independent. Particle aggregation may be induced by replacing a charged surface species with an uncharged adsorbate (Ref: Moskovits, *J. Phys. Chem. B*, 2005, 109, 14755) and it is envisaged that the overall negative charge due to the adsorbed conjugate results in electrostatic repulsion between particles and prevents the formation of larger aggregates.

Example 7

Preparation of Polyvalent Macromolecule By Polymerisation

Dyes can be of such a form that they can be directly incorporated into the polymer chain as a monomer (a polymerisable dye). As well as providing for very flexible polymer chemistry, this also facilitates polymer synthesis in situ by, for example, by attaching the dye to the surface and then carrying out the polymerisation. In the light of the present disclosure the skilled person would readily provide suitable methods for incorporating a dye into a polymer chain.

Figure 16A:
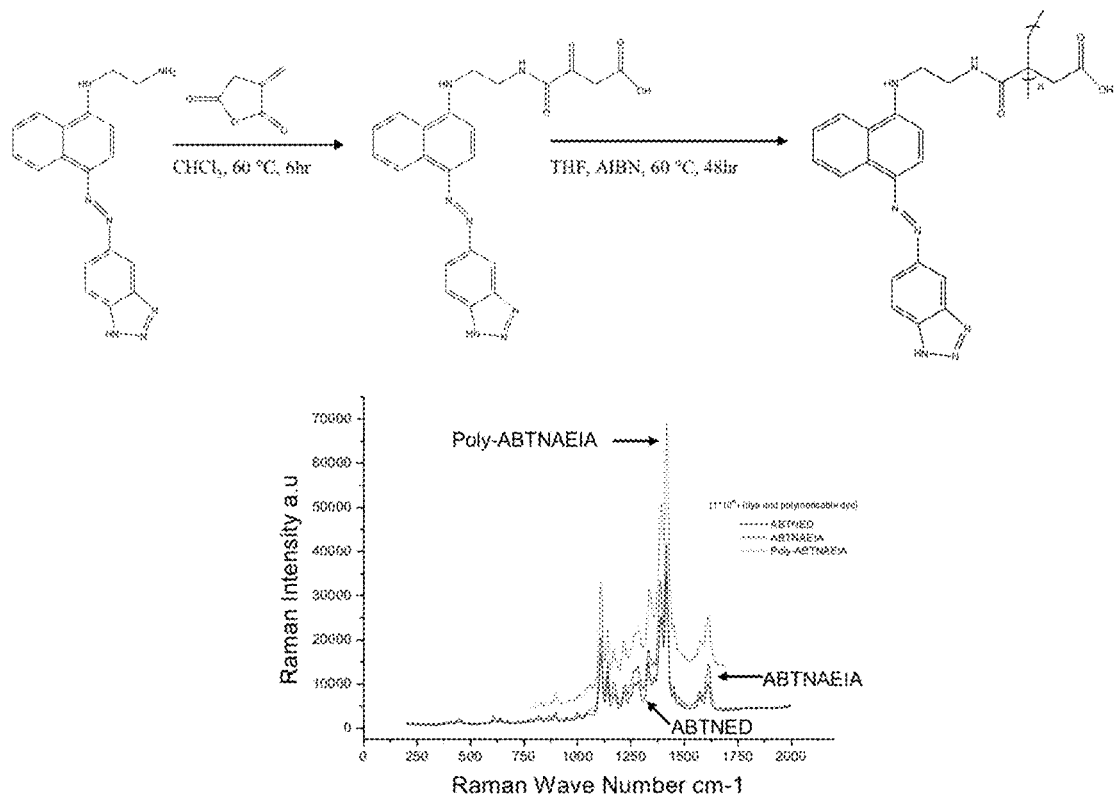
FIG. 16A: Scheme showing polymerisation of dyes as described in the Examples below. Inset: Representative SERRS spectra of reactants and products.
Figure 16B:
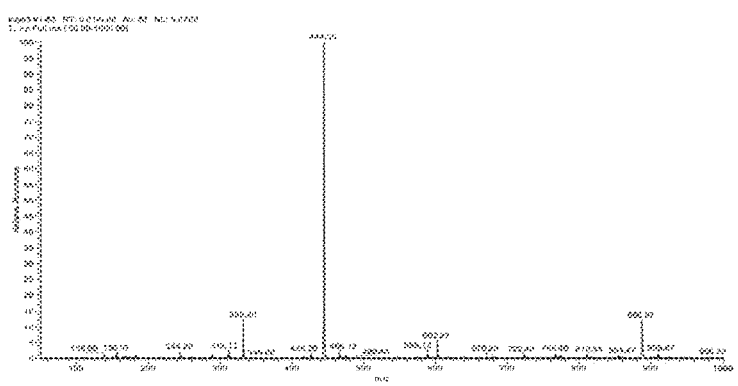
FIG. 16B: shows the mass spectrum of the polymerisable dye.

Synthesis of N-[4-(-5'-azobenzotriazolyl)naphthalen-1-yl)aminoethyl]-itaconamide and its homopolymer A scheme is shown in FIG. 16.

The example shows that a Raman active homopolymer dye (or copolymer dye) can be prepared from polymerisable Raman active dye, which in itself can be prepared by reacting Raman active dyes with reactive vinyl (or other polymerisable) monomers. T Itaconic anhydride (100 mg, 0.89 mmol), N-[4-(-5'-azobenzotriazolyl)naphthalen-1-yl)ethylene diamine hydrochloride (328 mg, 0.89 mmol) and triethylamine (90 mg, 0.89 mmol) were taken in dry chloroform (7.5 ml) and stirred at 60° C. in an oil bath for about 6 h. The triethylamine was used to neutralize the dye. After the reaction, chloroform was removed using a rotary evaporator. The residue was dissolved in ethyl acetate and separated by simple organic separation. The yield was 37%. (400 MHz; Acetone-d6) 3.55 (2H, CH2COO), 3.71 (2H, CH2NHCO), 3.79 (2H, CH2NH), 5.92 (1H, CH) 6.55 (1H, CH), 6.84 (1 H, ArH), 7.54 (1H, ArH), 7.66 (1H, ArH), 8.00 (1H, ArH), 8.08 (1H, ArH), 8.16 (1H, ArH), 8.21 (1H, ArH), 8.38 (1H, ArH) 9.10 (1H, ArH). M/z (LC/DI) 444.20.

The homopolymer of the N-[4-(-5'-azobenzotriazolyl) naphthalen-1-yl)aminoethyl]-itaconamide was obtained by solution polymerisation, the polymerisable dye ( 50 mg 0.011 mmol) along with 2.7 mg of 2,2 azobis-(2-methylpropionitrile) were dissolved in 5 ml of dry tetrahydrofuran and the contents were de-aerated by bubbling nitrogen. The reaction mixture was stirred at 60° C. for 48 hr. The product was separated out during the reaction and product was washed with methanol to remove the unreacted polymerisable dye. The yield was about 10%. The homopolymer was confirmed by disappearance of vinyl proton peaks [5.74 (1H, CH) and 5.95 (1H, CH)] and the appearance of broad peaks around 0.7 to 1.77 ppm.

The invention claimed is:

1. A polyvalent macromolecule comprising:
   (a) a polymer backbone and
   (b) two or more pendent groups attached to said polymer backbone,
   wherein at least two of said pendent groups each comprise:
   a surface-seeking group selected from a thiol, triazole, polyhydroxide, or a phosphorus or selenium containing group, which is capable of binding to a metal nanoparticle surface by chemisorption; and wherein at least two of said pendent groups each comprise a SERRS-active chromophore,
   wherein said polymer backbone is synthetic and is selected from the group consisting of polyanhydrides, polymethacrylates, polyacrylates, polyacrylamides, polystyrenes, polyvinylchloride, polyvinylacetate, polyvinylpyrrolidone, polyethers, poly(ethylene), polycyanoacrylates, polyesters, polyamides, polysiloxanes, polyorthoesters, polycarbonates, polyurethanes; and co-polymers thereof, wherein the polymer backbone is not a polypeptide, polysaccharide or polynucleotide, wherein said polyvalent macromolecule is capable of binding two or more metal nanoparticles, promoting aggregation of said two or more metal nanoparticles, and stabilising metal nanoparticle aggregates once formed.

2. A polyvalent macromolecule according to claim 1, wherein said polymer backbone is a co-polymer.

3. A polyvalent macromolecule according to claim 2, wherein said polymer backbone is poly(styrene-co-maleic anhydride).

4. A polyvalent macromolecule according to claim 1 wherein the surface-seeking group and the chromophore are present on the same pendent group.

5. A polyvalent macromolecule according to claim 1 wherein said surface seeking group comprises a benzotriazole group.

6. A polyvalent macromolecule according to claim 1, wherein said chromophore comprises an azo group (—N═N—).

7. A polyvalent macromolecule according to claim 1, further comprising a linker, wherein said linker is bound to the polymer backbone covalently.

8. A polyvalent macromolecule according to claim 7 wherein said linker is selected from the group consisting of $C_{1-10}$ alkylene, $C_{5-20}$ arylene, and -A-$(CH_2)_n$—B—, where A and B are each independently selected from: a direct bond, $CH_2$, O, S, NR, where n is an integer from 0 to 5 and R represents H or $C_{1-5}$ alkyl.

9. A polyvalent macromolecule according to claim 8 wherein said linker is selected from —NH—$(CH_2)_n$—NH— where n is from 1 to 5.

10. A polyvalent macromolecule according to claim 1, wherein said pendent groups are of general formula 3:

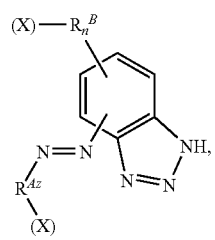

wherein n is 0, 1, 2 or 3; and wherein one of $R^B$ or $R^{AZ}$ is bonded to X, where X is a linker.

11. A polyvalent macromolecule according to claim 10, wherein the pendent groups are selected from compounds of formulae 3A and 3C:

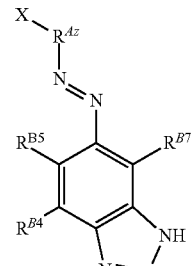

3A

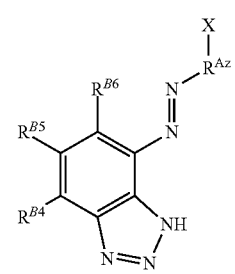

3C wherein each of $R^{B4}$, $R^{B5}$, $R^{B6}$ and $R^{B7}$ is independently H or a benzo substituent.

12. A polyvalent macromolecule according to claim 10, wherein $R^{AZ}$ is selected from optionally substituted $C_{5-20}$ aryl and is a group of formula:

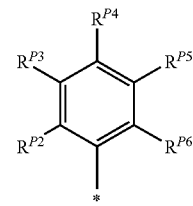

wherein each of $R^{P2}$, $R^{P3}$, $R^{P4}$, $R^{P5}$ and $R^{P6}$ is independently selected from:
the linker X, —H, -halo, $C_{1-7}$ alkyl, $C_{3-10}$ cycloalkyl, $C_{5-20}$ aryl, —C(O)R, —$CO_2$H, —C(O)$NR_2$, —OR, —$NR_2$, —$N_3$, —NO, —$NO_2$, —CN, —CH═NR, —C═N(OH)R, —NHC(═O)NHR, —NHC(═S)NHR, —NHC(═O)R, —OP(═O)(OR)$_2$, —$SiR_3$, —SR, —SSR, —$SO_3$H, —SeR, —$SnR_3$, and —$PbR_3$, wherein each R is independently H, $C_{1-7}$ alkyl, $C_{3-10}$ cycloalkyl or $C_{5-20}$ aryl;
or two adjacent groups selected from $R^{P2}$, $R^{P3}$, $R^{P4}$, $R^{P5}$ and $R^{P6}$, together with the atoms to which they are attached, form a fused $C_{5-6}$ aryl ring, which may optionally be substituted; and the remaining groups from $R^{P2}$, $R^{P3}$, $R^{P4}$, $R^{P5}$ and $R^{P6}$ are as previously defined.

13. A polyvalent macromolecule according to claim 10, wherein the linker X is selected from the group consisting of $C_{1-10}$ alkylene, $C_{5-20}$ arylene, and -A-$(CH_2)_n$—B—, where A and B are each independently selected from: a direct bond, $CH_2$, O, S, NR, where n is an integer from 0 to 5 and R represents H or $C_{1-5}$ alkyl.

14. A polyvalent macromolecule according to claim 13, wherein the linker X is selected from —NH—$(CH_2)_n$—NH— where n is from 1 to 5.

15. A polyvalent macromolecule according to claim 1, further comprising a linker, wherein the linker is attached between the chromophore and the surface seeking group.

16. A polyvalent macromolecule according claim 1, wherein said pendent groups are of the formula 3B-i

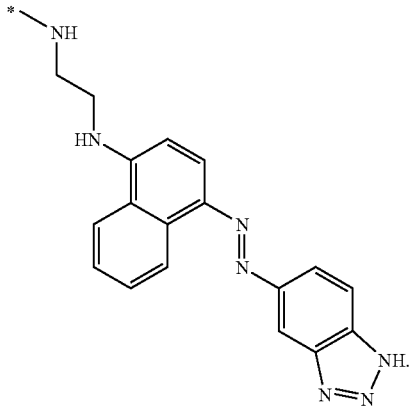

3B-i

17. A polyvalent macromolecule according to claim 1, comprising at least two different pendent groups attached to said polymer backbone.

18. A polyvalent macromolecule according to claim 1, further comprising at least one attached biomolecule.

19. A polyvalent macromolecule according to claim 18, wherein said biomolecule is selected from the group consisting of proteins, enzymes, antibodies, polypeptides, peptides, amino acids, polysaccharides, nucleic acids, oligonucleotides, DNA, RNA, lipids, phospholipids, glycolipids, co-factors, hormones, vitamins, and neurotransmitters.

20. A polyvalent macromolecule according to claim 1, wherein said polyesters are selected from polylactide, polyglycolide, and polycaprolactone.

21. A polyvalent macromolecule according to claim 1, wherein the metal nanoparticle surface is selected from gold, silver, copper, iron and aluminum.

22. A polyvalent macromolecule according to claim 1, wherein the surface-seeking group is selected from a calixarene, a mercaptobenzotriazole, and a polyphosphate.

* * * * *